(12) United States Patent
Gatayama et al.

(10) Patent No.: US 11,717,242 B2
(45) Date of Patent: Aug. 8, 2023

(54) PHOTON COUNTING COMPUTED TOMOGRAPHY (CT) APPARATUS

(71) Applicant: CANON MEDICAL SYSTEMS CORPORATION, Tochigi (JP)

(72) Inventors: Kazuki Gatayama, Otawara (JP); Kusuto Koga, Utsunomiya (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 118 days.

(21) Appl. No.: 17/488,940

(22) Filed: Sep. 29, 2021

(65) Prior Publication Data

US 2022/0096028 A1    Mar. 31, 2022

(30) Foreign Application Priority Data

Sep. 30, 2020   (JP) .................................. 2020-165483

(51) Int. Cl.
*A61B 6/00* (2006.01)
*A61B 6/03* (2006.01)

(52) U.S. Cl.
CPC ............ *A61B 6/4241* (2013.01); *A61B 6/032* (2013.01); *A61B 6/482* (2013.01)

(58) Field of Classification Search
CPC ....... A61B 6/4241; A61B 6/032; A61B 6/482; A61B 6/5205; G01T 1/17
See application file for complete search history.

(56) References Cited

U.S. PATENT DOCUMENTS

| 7,583,779 B2 | 9/2009 | Tkaczyk et al. |
| 9,841,389 B2 | 12/2017 | Tamura et al. |
| 2014/0233693 A1* | 8/2014 | Wang ..................... A61B 6/582 378/207 |
| 2018/0038969 A1 | 2/2018 | McCollough et al. |
| 2020/0033273 A1 | 1/2020 | Moriyasu et al. |

\* cited by examiner

*Primary Examiner* — Courtney D Thomas
(74) *Attorney, Agent, or Firm* — Oblon, McClelland, Maier & Neustadt, L.L.P.

(57) ABSTRACT

A photon counting computed tomography (CT) apparatus according to an embodiment includes a photon counting detector and processing circuitry. The photon counting detector detects X-ray photons to acquire energy information. The processing circuitry acquires at least one piece of information out of information on an imaging mode, information on a site to be imaged, and information on a medical device. The processing circuitry, based on the acquired information, determines at least one condition out of a condition on an energy band of data collected by the photon counting detector and a condition on an energy band for data for use in reconstruction processing out of the data collected by the photon counting detector.

6 Claims, 14 Drawing Sheets

| IMAGING MODE | ENERGY BAND |
|---|---|
| MONITORING SCAN | ENERGY VALUE 41b TO 41c |
| HELICAL SCAN IN FULL SCAN | ENERGY VALUE 41a TO 41b, 41b TO 41c, 41c TO 41d, 41d TO 41e, 41e TO 41f, 41f TO 41g |
| ⋮ | ⋮ |

35a

LOWER ENERGY → HIGHER ENERGY 41b, 41c, 41d
40b, 40c

LOWER ENERGY → HIGHER ENERGY 41b, 41c, 41d, 41e, 41f
40b, 40d, 40e

| MEDICAL DEVICE | ENERGY BAND |
|---|---|
| PUNCTURE NEEDLE | ENERGY VALUE 41b TO 41c, 41c TO 41d |
| ⋮ | ⋮ |

| SITE TO BE IMAGED | ENERGY BAND |
|---|---|
| CHEST | ENERGY VALUE 41a TO 41b |
| HEAD | ENERGY VALUE 41c TO 41d |
| ⋮ | ⋮ |

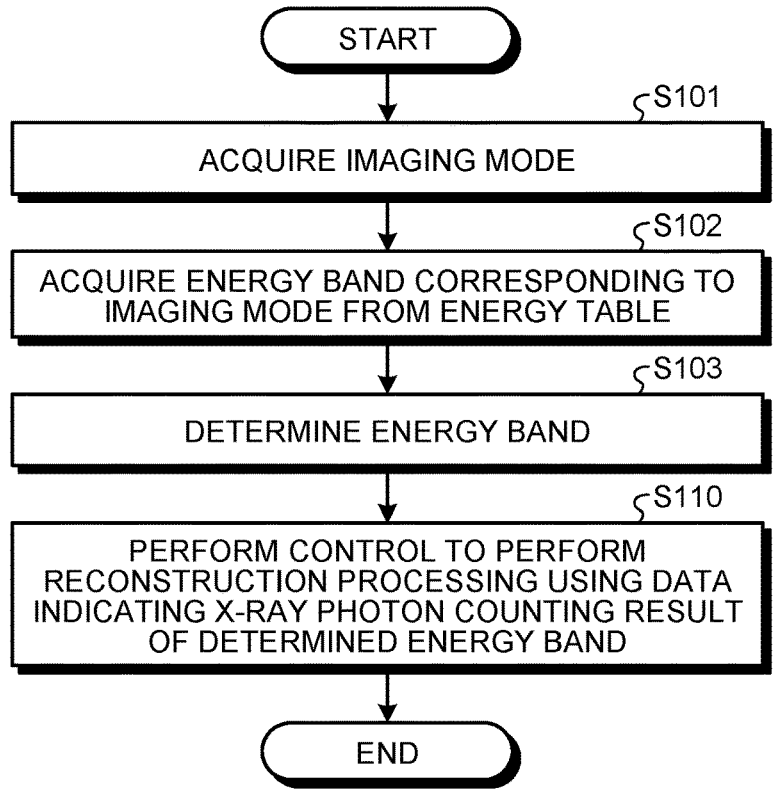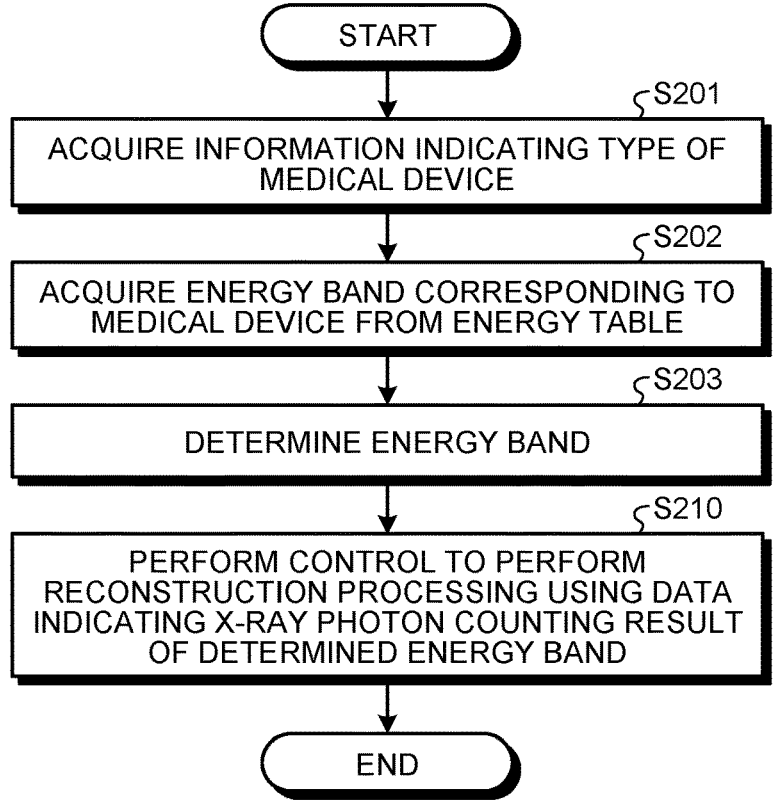

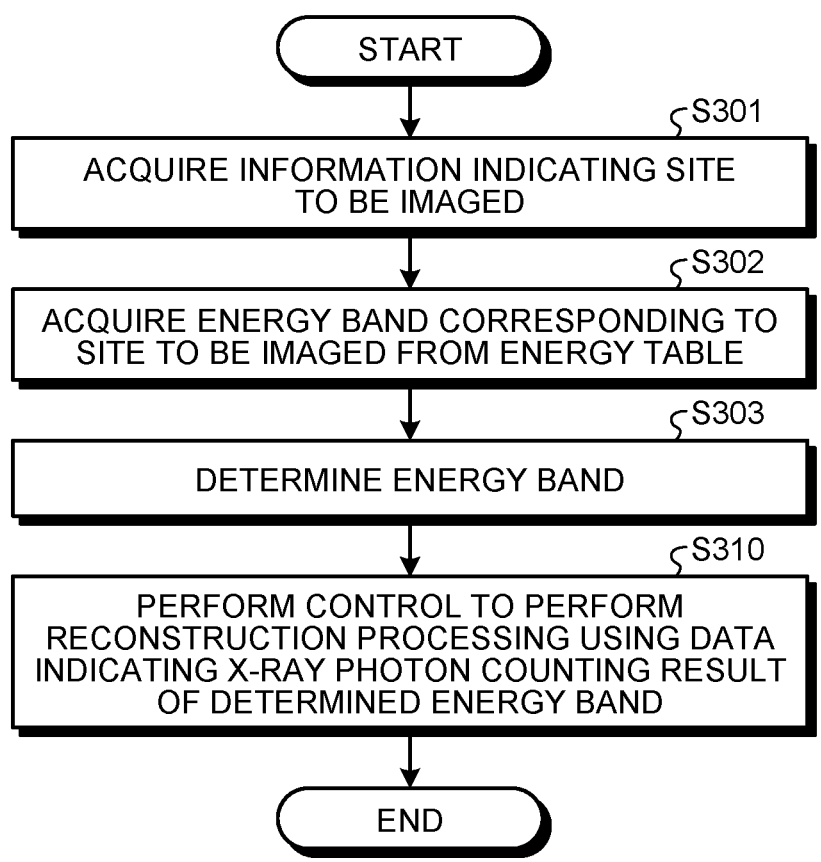

| RECONSTRUCTION CONDITION | ENERGY BAND |
|---|---|
| AA | ENERGY VALUE 41b TO 41c |
| BB | ENERGY VALUE 41c TO 41d |
| ⋮ | ⋮ |

PHOTON COUNTING COMPUTED TOMOGRAPHY (CT) APPARATUS

CROSS-REFERENCE TO RELATED APPLICATIONS

This application is based upon and claims the benefit of priority from Japanese Patent Application No. 2020-165483, filed on Sep. 30, 2020; the entire contents of which are incorporated herein by reference.

FIELD

Embodiments disclosed herein relate generally to a photon counting computed tomography (CT) apparatus.

BACKGROUND

There have conventionally been X-ray CT apparatuses performing CT imaging using one kind of tube voltage (kv) and collecting data collected by the tube voltage and a tube current (mA) set in advance of an X-ray tube (bulb). An X-ray CT apparatus collects two kinds of fixed energy information using one kind of tube voltage, for example. The X-ray CT apparatus may perform imaging using two kinds of tube voltages such as dual energy imaging depending on clinical purposes. In both cases of the case in which one kind of tube voltage is used and the case in which two kinds of tube voltages are used, imaging conditions mainly include the tube voltage and the tube current.

Photon counting CT imaging can collect any plurality of pieces of information on energy (energy information) by an X-ray detector.

BRIEF DESCRIPTION OF THE DRAWINGS

FIG. 18 is a flowchart of an example of a procedure of fourth energy band determination processing that the X-ray CT apparatus according to a third embodiment executes;

FIG. 19 is a flowchart of an example of a procedure of fifth energy band determination processing that the X-ray CT apparatus according to the third embodiment executes;

FIG. 20 is a flowchart of an example of a procedure of sixth energy band determination processing that the X-ray CT apparatus according to the third embodiment executes;

DETAILED DESCRIPTION

One of the problems to be solved by embodiments disclosed in the present specification and drawings is to determine an optimum energy band in accordance with an imaging mode, a site to be imaged, or the type of a medical device. However, the problems to be solved by the embodiments disclosed in the present specification and drawings are not limited to the problem. Problems corresponding to effects by configurations shown in the embodiments described below can be regarded as the other problems.

A photon counting computed tomography (CT) apparatus according to an embodiment includes a photon counting detector and processing circuitry. The photon counting detector detects X-ray photons to acquire energy information. The processing circuitry acquires at least one piece of information out of information on the imaging mode, information on the site to be imaged, and information on the medical device. The processing circuitry, based on the acquired information, determines at least one condition out of a condition on an energy band of data collected by the photon counting detector and a condition on an energy band for data for use in reconstruction processing out of the data collected by the photon counting detector.

The following describes X-ray CT apparatuses according to the embodiments with reference to the accompanying drawings. Note that details described for one embodiment or one modification are in principle applied to other embodiments and other modifications in the same way.

First Embodiment

Figure 1:
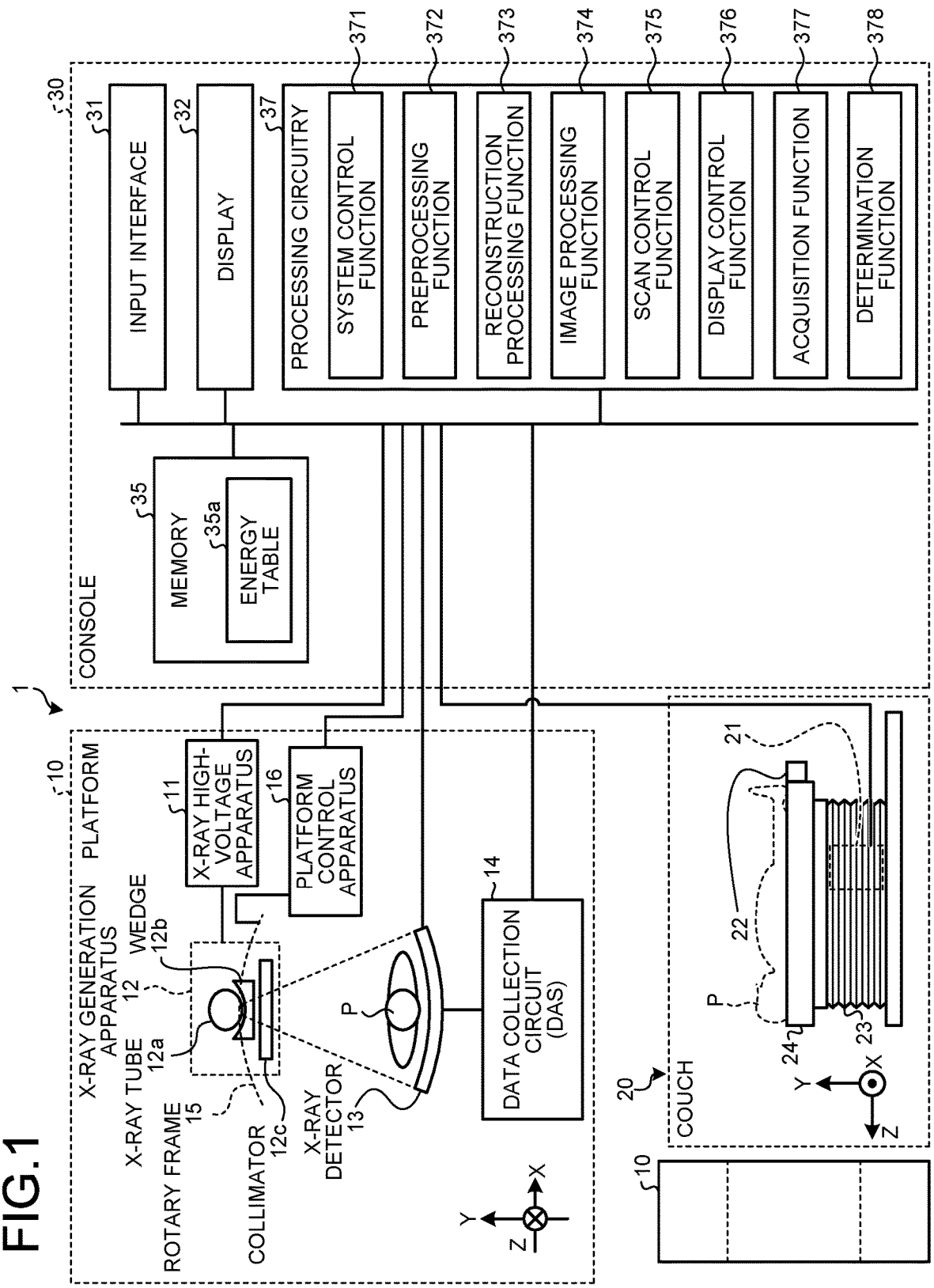
FIG. 1 is a diagram of a configuration example of an X-ray computed tomography (CT) apparatus according to a first embodiment.

FIG. 1 is a diagram of a configuration example of an X-ray CT apparatus 1 according to a first embodiment. The X-ray CT apparatus 1 is a photon counting X-ray CT apparatus that can execute photon counting CT. That is to say, the X-ray CT apparatus 1 is an apparatus that counts X-ray photons having passed through a subject P using a photon counting type photon counting detector, not a conventional integral type (current mode measurement type) detector, and can thereby reconstruct X-ray CT image data with a high S/N ratio. As illustrated in FIG. 1, the X-ray CT apparatus 1 according to the first embodiment has a platform 10, a couch 20, and a console 30.

The platform 10 is an apparatus applying X-rays to the subject P to collect data on X-rays having passed through the subject P. The platform 10 has an X-ray high-voltage apparatus 11, an X-ray generation apparatus 12, an X-ray detector 13, a data collection circuit 14, a rotary frame 15, and a platform control apparatus 16. In the platform 10, as illustrated in FIG. 1, a Cartesian coordinate system consisting of an X axis, a Y axis, and a Z axis is defined. That is to say, the X axis indicates a horizontal direction, the Y axis indicates a vertical direction, and the Z axis indicates a rotary central axial direction of the rotary frame 15 when the platform 10 is in a non-tilt state.

The rotary frame 15 is an annular frame supporting the X-ray generation apparatus 12 and the X-ray detector 13 such that they face each other across the subject P and rotating at high speed on a circular orbit about the subject P by the platform control apparatus 16 described below.

The X-ray generation apparatus 12 is an apparatus generating X-rays and applying the generated X-rays to the subject P. The X-ray generation apparatus 12 has an X-ray tube (bulb) 12a, a wedge 12b, and a collimator 12c.

The X-ray tube 12a is a vacuum tube receiving supply of high voltage from the X-ray high-voltage apparatus 11 to apply thermoelectrons from a cathode (may also be called a filament) toward an anode (target). The X-ray tube 12a applies an X-ray beam to the subject P along with the rotation of the rotary frame 15. That is to say, the X-ray tube 12a generates X-rays using the high voltage supplied from the X-ray high-voltage apparatus 11.

The X-ray tube 12a generates an X-ray beam spreading with a fan angle and a cone angle. The X-ray tube 12a can continuously emit X-rays in the total circumference of the subject P for full reconstruction or can continuously emit X-rays in an emission range enabling half reconstruction, or 180 degrees+the fan angle, for half reconstruction by the control of the X-ray high-voltage apparatus 11, for example. The X-ray tube 12a can intermittently emit X-rays (pulsed X-rays) at a position (a bulb position) set in advance by the control of the X-ray high-voltage apparatus 11. The X-ray high-voltage apparatus 11 can modulate the intensity of the X-rays emitted from the X-ray tube 12a. The X-ray high-voltage apparatus 11 increases the intensity of the X-rays emitted from the X-ray tube 12a at a specific bulb position and reduces the intensity of the X-rays emitted from the X-ray tube 12a in the range other than the specific bulb position, for example.

The wedge 12b is an X-ray filter for adjusting an X-ray dose of the X-rays emitted from the X-ray tube 12a. Specifically, the wedge 12b is a filter passing the X-rays emitted from the X-ray tube 12a and attenuating the X-rays such that the X-rays applied from the X-ray tube 12a to the subject P will have distribution set in advance. The wedge 12b is a filter made by processing aluminum so as to have a certain target angle and a certain thickness, for example. The wedge is also called a wedge filter or a bow-tie filter.

The collimator 12c is formed of a lead plate or the like and has a slit in part thereof. The collimator 12c narrows down the application range of the X-rays the X-ray dose of which has been adjusted by the wedge 12b by the slit by the control of the X-ray high-voltage apparatus 11 described below, for example.

The X-ray source of the X-ray generation apparatus 12 is not limited to the X-ray tube 12a. The X-ray generation apparatus 12 may include a focus coil converging an electron beam generated from an electron gun, a deflection coil electromagnetically deflecting the electron beam, and a target ring surrounding the half circumference of the subject P and colliding with the deflected electron beam to generate X-rays in place of the X-ray tube 12a, for example.

The X-ray high-voltage apparatus 11 includes a high-voltage generation apparatus including a transformer and an electric circuit such as a rectifier and has a function of generating high voltage to be applied to the X-ray tube 12a and an X-ray control apparatus performing control of output voltage corresponding to the X-rays to be applied by the X-ray tube 12a. The high-voltage generation apparatus may be of a transformer system or of an inverter system. The X-ray high-voltage apparatus 11 adjusts a tube voltage or a tube current to be supplied to the X-ray tube 12a to adjust an X-ray dose to be applied the subject P, for example. The X-ray high-voltage apparatus 11 receives control from processing circuitry 37 of the console 30.

The platform control apparatus 16 includes processing circuitry including a central processing unit (CPU) and a drive mechanism such as a motor and an actuator. The platform control apparatus 16 has a function of receiving an input signal from an input interface 31 mounted on the console 30 or an input interface mounted on the platform 10 to perform operation control of the platform 10. The platform control apparatus 16 performs control to turn the X-ray tube 12a and the X-ray detector 13 on the circular orbit about the subject P by receiving the input signal to rotate the rotary frame 15, control to tilt the platform 10, and control to operate the couch 20 and a couchtop 22, for example. The platform control apparatus 16 receives control from the processing circuitry 37 of the console 30.

The X-ray detector 13 is an example of a photon counting detector that includes a plurality of detection elements and outputs a signal corresponding to a counted number of X-ray photons. The X-ray detector 13 includes a plurality of X-ray detection element rows in which a plurality of X-ray detection elements (also referred to as "sensors" or simply as "detection elements") are arranged in a channel direction along an arc with the focus of the X-ray tube 12a as the center, for example. The X-ray detector 13 has a structure in which the X-ray detection element rows in which the X-ray detection elements are arranged in the channel direction are arranged in slice direction. Each of the X-ray detection elements of the X-ray detector 13 detects the X-rays applied from the X-ray generation apparatus 12 to have passed through the subject P and outputs an electric signal (pulse) corresponding to the X-ray dose. The electric signal output by each of the X-ray detection elements is also referred to as a detection signal.

Figure 2:
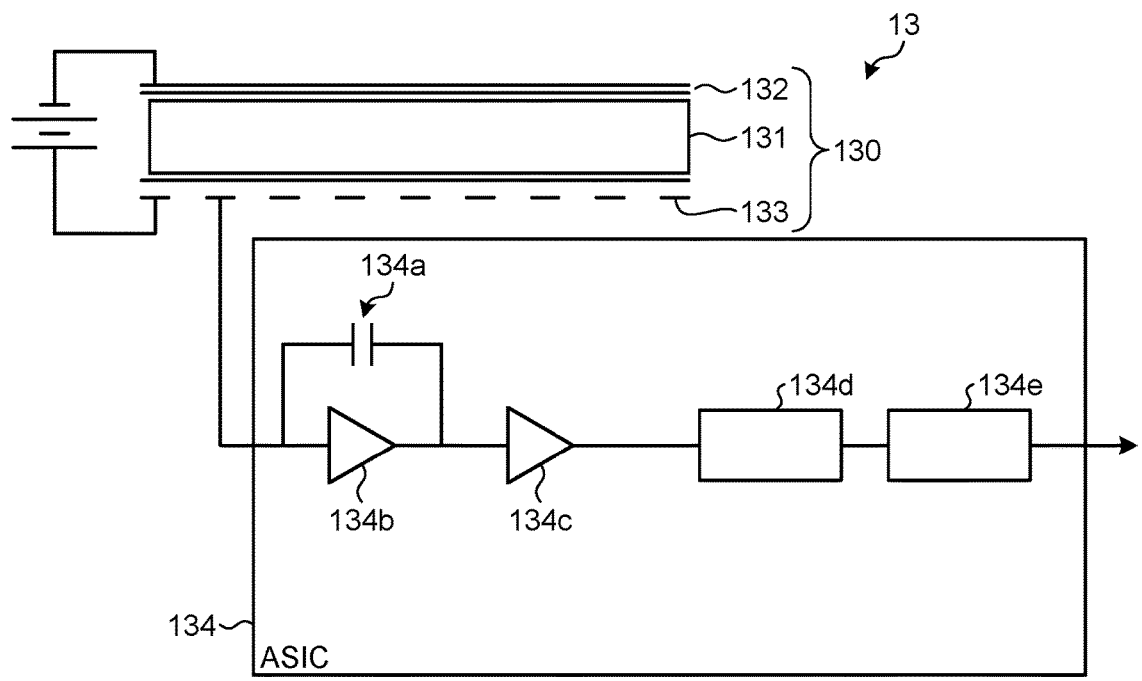
FIG. 2 is a diagram for illustrating an X-ray detector according to the first embodiment.

FIG. 2 is a diagram for illustrating the X-ray detector 13 according to the first embodiment. The X-ray detector 13 is a direct conversion type photon counting detector, for example.

As illustrated in FIG. 2, the X-ray detector 13 is a photon counting detector having a plurality of detectors each including a detection element (an X-ray detection element) 130 detecting X-ray photons and an application specific integrated circuit (ASIC) 134 connected to the detection element 130 and counting the X-ray photons detected by the detection element 130. The example in FIG. 2 illustrates one detector among the detectors.

The detection element 130 has a semiconductor 131, a cathode electrode 132, and a plurality of anode electrodes 133. The semiconductor 131 is a semiconductor such as cadmium telluride (CdTe) or zinc cadmium telluride (CZT). Each of the anode electrodes 133 corresponds to an individual detection pixel (also referred to as a "pixel"). When X-ray photons are made incident, the detection element 130 directly converts the X-rays made incident on the detection element 130 into charges and outputs the charges to the ASIC 134.

The ASIC 134 discriminates the individual charges output by the detection element 130 to count the number of the X-ray photons made incident on the detection element 130. The ASIC 134 performs computation processing based on the magnitude of the individual charges to measure the energy of the counted X-ray photons. The ASIC 134 has a capacitor 134a, an amplifier circuit 134b, a waveform shaping circuit 134c, a comparator circuit 134d, and a counter 134e, for example. The ASIC 134 is an example of a counting circuit.

The capacitor 134a accumulates the charges output by the detection element 130. The amplifier circuit 134b is a circuit integrating and amplifying the charges collected in the capacitor 134a and outputting the charges as a pulse signal of the amount of electricity in response to the X-ray photons made incident on the detection element 130. The wave height or the area of this pulse signal has correlation with photon energy.

The amplifier circuit 134b includes an amplifier, for example. The amplifier is a single-ended type amplifier, for example. When the amplifier is the single-ended type amplifier, the amplifier is grounded and amplifies the potential difference between a ground potential (ground) and a potential indicated by the electric signal output by the detection element 130. The amplifier may be a differential amplifier. When the amplifier is the differential amplifier, a positive input (+) of the amplifier is connected to the detection element 130, whereas a negative input (−) thereof is grounded. The differential amplifier amplifies the potential difference between a potential indicated by the electric signal from the detection element 130 input to the positive input and a ground potential indicated by a signal input to the negative input.

The waveform shaping circuit 134c is a circuit adjusting the frequency characteristics of the pulse signal output from the amplifier circuit 134b and giving a gain and an offset thereto to shape the waveform of the pulse signal.

The comparator circuit 134d is a circuit comparting the wave height or the area of a response pulse signal to the incident photons with a threshold set in advance in accordance with a plurality of energy bands to be discriminated from each other and outputting a comparison result with the threshold to the following counter 134e.

The counter 134e counts a discrimination result of the waveform of the response pulse signal for each corresponding energy band and outputs a photon counting result as digital data to the data collection circuit 14. The counter 134e generates digital data indicating X-ray photon counting results of the respective energy bands and outputs the generated digital data to the data collection circuit 14, for example.

With the configuration described above, the X-ray detector 13 detects the X-ray photons to acquire the energy information. The X-ray detector 13 may be an indirect conversion type photon counting detector including a grid, a scintillator array, and an optical sensor array, for example. The scintillator array includes a plurality of scintillators, and the scintillators include scintillator crystals outputting pieces of light of the number corresponding to incident X-ray energy. The grid is placed on an X-ray incident side face of the scintillator array and includes an X-ray shielding plate having a function of absorbing scattered X-rays. The optical sensor array has a function of converting light from the scintillators into an electric signal corresponding to the light amount from the scintillators and includes optical sensors such as photomultiplier tubes, for example. The optical sensors are photodiodes (PDs), avalanche photodiodes (APDs), silicon photomultipliers (SiPM), or the like, for example.

Figure 3:
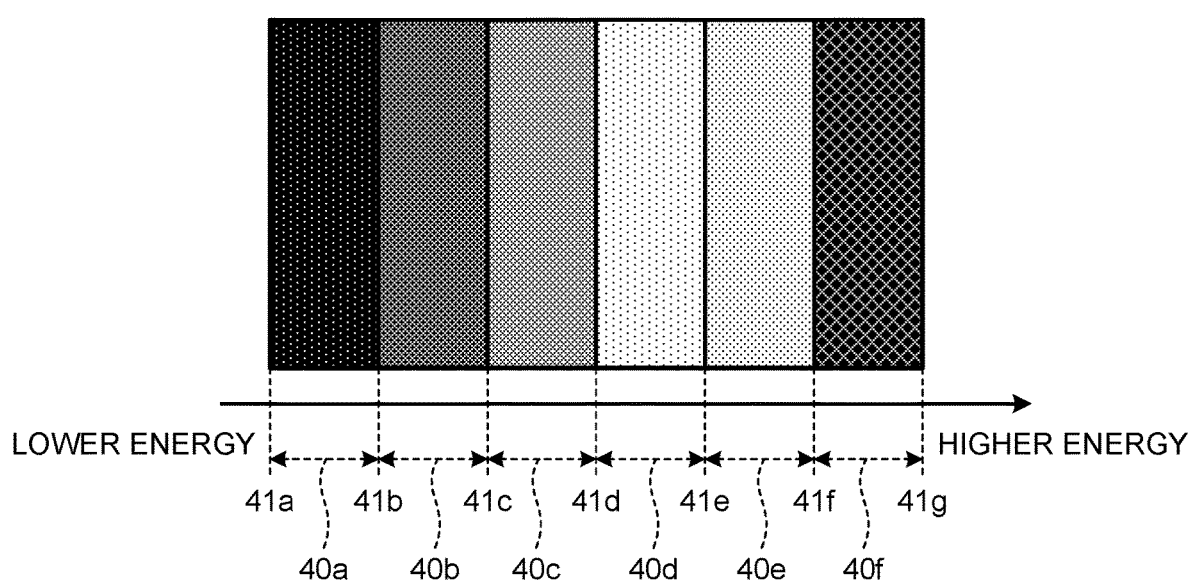
FIG. 3 is a diagram of an example of a plurality of energy bands that can be used when the X-ray detector according to the first embodiment generates digital data.

FIG. 3 is a diagram of an example of a plurality of energy bands that can be used when the X-ray detector 13 according to the first embodiment generates digital data. The X-ray detector 13 can use six energy bands 40a to 40f when generating the digital data, for example.

In the example in FIG. 3, the energy band 40a is an energy band within a range of a value of energy (an energy value) 41a or more and less than an energy value 41b. The energy band 40b is an energy band within a range of the energy value 41b or more and less than an energy value 41c. The energy band 40c is an energy band within a range of the energy value 41c or more and less than an energy value 41d. The energy band 40d is an energy band within a range of the energy value 41d or more and less than an energy value 41e. The energy band 40e is an energy band within a range of the energy value 41e or more and less than an energy value 41f. The energy band 40f is an energy band within a range of the energy value 41f or more and less than an energy value 41g.

That is to say, the boundary between the energy band 40a and the energy band 40b, which are two energy bands adjacent to each other, is indicated by the energy value 41b. The same applies to the boundary between other two energy bands adjacent to each other.

In the first embodiment, the X-ray detector 13, receiving control by the processing circuitry 37, sets an energy band used when generating the digital data out of the six energy bands 40a to 40f. The X-ray detector 13 sets the one energy band 40b or sets the six energy bands 40a to 40f, for example.

In the first embodiment, the widths of the respective six energy bands 40a to 40f are fixed values. Furthermore, in the first embodiment, the energy values indicating the boundaries between two energy bands adjacent to each other are also fixed values. Thus, the X-ray detector 13 cannot change the widths of the respective six energy bands 40a to 40f. The X-ray detector 13 cannot change the energy values indicating the boundaries between two energy bands adjacent to each other either. Furthermore, the X-ray detector 13 cannot newly set any energy bands. That is to say, in the first embodiment, the X-ray detector 13 cannot set any optional energy bands.

Referring back to the description of FIG. 1, the data collection circuit 14 (data acquisition system (DAS)) is a circuit collecting counting processing results from respective detection elements 130 of the X-ray detector 13 to generate detection data (projection data). In other words, the data collection circuit 14 collects a counting result by the X-ray detector 13. The detection data is a sinogram, for example. The sinogram is data in which the counting processing results made incident on the respective detection elements 130 are arranged at each position of the X-ray tube 12a. That is to say, the sinogram indicates counting results of the respective energy bands of the X-ray photons made incident on the respective detection elements 130 at each position of the X-ray tube 12a. The data collection circuit 14 collects counting processing results at respective view angles from the X-ray detector 13 to generate the sinogram.

The couch 20 is an apparatus carrying and moving the subject P to be scanned and includes a couch driving apparatus 21, the couchtop 22, a base stand 23, and a base (support frame) 24.

The couchtop 22 is a plate on which the subject P is placed. The base 24 supports the couchtop 22. The base stand 23 is a casing supporting the base 24 in a movable manner in the vertical direction. The couch driving apparatus 21 is a motor or an actuator moving the couchtop 22 on which the subject P is placed in a long axial direction of the couchtop 22 to move the subject P into the rotary frame 15. The couch driving apparatus 21 can also move the couchtop 22 in an X-axial direction.

The method for moving the couchtop may move only the couchtop 22 or may be a system moving the couchtop 22 together with the base 24 of the couch 20. In the case of an upright CT, a system moving a patient moving mechanism corresponding to the couchtop 22 may be employed.

The platform 10 executes helical scan, which rotates the rotary frame 15 while moving the couchtop 22 to helically scan the subject P, for example. Alternatively, the platform 10 executes conventional scan, which moves the couchtop 22 and then rotates the rotary frame 15 with the position of the subject P fixed to scan the subject P in a circular orbit. Although in the description of the following embodiments a relative position change of the platform 10 and the couchtop 22 is implemented by controlling the couchtop 22, the embodiments are not limited to this example. When the platform 10 is of a mobile type, for example, the relative position change of the platform 10 and the couchtop 22 may be implemented by controlling the traveling of the platform 10. Alternatively, the relative position change of the platform 10 and the couchtop 22 may be implemented by controlling the traveling of the platform 10 and the couchtop 22.

The console 30 is an apparatus receiving operations on the X-ray CT apparatus 1 by an operator and reconstructing X-ray CT image data using the sinogram (the counting result) collected by the platform 10. As illustrated in FIG. 1, the console 30 has an input interface 31, a display 32, a memory 35, and processing circuitry 37.

The input interface 31 receives various kinds of input operations from the operator and converts the received input operations into electric signals to output the electric signals to the processing circuitry 37. The input interface 31 receives a collection condition when the projection data is collected, a reconstruction condition when the X-ray CT image data is reconstructed, an image processing condition when image data (postprocessed image data) is generated from the X-ray CT image data, and the like from the operator, for example. The input interface 31 is implemented by a mouse, a keyboard, a trackball, a switch, a button, a joystick, or the like, for example.

The display 32 displays various kinds of information. The display 32 outputs an image (an X-ray CT image) based on image data generated by the processing circuitry 37, a graphical user interface (GUI) for receiving various kinds of operations from the operator, and the like, for example. The display 32 includes a liquid crystal display or a cathode ray tube (CRT) display, for example.

The memory 35 is implemented by a semiconductor memory such as a random access memory (RAM) or a flash memory, a hard disk, an optical disc, or the like, for example. The memory 35 stores therein the projection data and reconstructed image data, for example. The memory 35 stores therein an energy table 35a. The memory 35 is an example of a storage unit. The energy table 35a will be described below.

The processing circuitry 37 executes a system control function 371, a preprocessing function 372, a reconstruction processing function 373, an image processing function 374, a scan control function 375, a display control function 376, an acquisition function 377, and a determination function 378, for example. Respective processing functions executed by the system control function 371, the preprocessing function 372, the reconstruction processing function 373, the image processing function 374, the scan control function 375, the display control function 376, the acquisition function 377, and the determination function 378 as components of the processing circuitry 37 illustrated in FIG. 1 are recorded in the memory 35 in the form of a computer-executable computer program, for example. The processing circuitry 37 is implemented by a processor, for example. The processing circuitry 37 reads the computer programs from the memory 35 and executes the read computer programs to implement functions corresponding to the respective computer programs. In other words, the processing circuitry 37 that has read the computer programs has the functions indicated within the processing circuitry 37 in FIG. 1.

The system control function 371 controls the various kinds of functions of the processing circuitry 37 based on the input operations received from the operator via the input interface 31.

The preprocessing function 372 performs preprocessing such as logarithmic conversion processing, offset correction processing, inter-channel sensitivity correction processing, inter-channel gain correction processing, pileup correction processing, response function correction processing, and beam hardening correction on the detection data output from the data collection circuit 14 to generate raw data. The preprocessing function 372 stores the raw data in the memory 35.

As described above, the data output from the data collection circuit 14 is referred to as the detection data, whereas the data obtained by performing the preprocessing such as logarithmic conversion processing, offset correction processing, inter-channel sensitivity correction processing, inter-channel gain correction processing, pileup correction processing, response function correction processing, and beam hardening correction on the detection data is referred to as the raw data. The detection data and the raw data are collectively referred to as the projection data.

The reconstruction processing function 373 performs reconstruction processing using filtered back projection, successive approximation reconstruction, or the like on the raw data generated by the preprocessing function 372 to generate the X-ray CT image data. The reconstruction processing function 373 stores the reconstructed X-ray CT image data in the memory 35.

The projection data generated from the sinogram (the counting result) obtained by the photon counting CT includes information on the energy of X-rays attenuated by being passed through the subject P. Thus, the reconstruction processing function 373 can reconstruct the X-ray CT image data of a specific energy component, for example. The reconstruction processing function 373 can reconstruct the pieces of X-ray CT image data of a plurality of respective energy components, for example.

The reconstruction processing function 373 generates image data with a color tone corresponding to an energy component assigned to each pixel of the X-ray CT image data of each energy component and with a plurality of pieces of X-ray CT image data sorted by color in accordance with the energy component superimposed on each other, for example. The reconstruction processing function 373 can generate image data that, using the K absorption end unique to a substance, can identify the substance, for example. Examples of other image data generated by the reconstruction processing function 373 include monochromatic X-ray image data, density image data, and effective atomic number image data.

As an application of X-ray CT, there is a technique discriminating the type, the amount of presence, the density, and the like of substances contained in the subject P using the fact that X-ray absorption characteristics vary by substance. This technique is referred to as substance discrimination. The reconstruction processing function 373 performs substance discrimination on the projection data to obtain substance discrimination information, for example. The reconstruction processing function 373 reconstructs substance discrimination image data indicating a substance discrimination image using the substance discrimination information as a result of substance discrimination.

When reconstructing the X-ray CT image data, the reconstruction processing function 373 can use a full scan reconstruction system and a half scan reconstruction system. In the full scan reconstruction system, the reconstruction processing function 373 needs the projection data for the circumference of the subject, or 360 degrees, for example. In the half scan reconstruction system, the reconstruction processing function 373 needs the projection data for 180 degrees+the fan angle. In the following, to make the description simple, it is assumed that the reconstruction processing function 373 uses the full scan reconstruction system, which performs reconstruction using the projection data for the circumference of the subject, or 360 degrees.

The image processing function 374 converts the X-ray CT image data generated by the reconstruction processing function 373 into various kinds of image data such as tomographic image data of any section and three-dimensional image data by rendering processing by known methods based on an input operation received from the operator via the input interface 31. When the scan control function 375 executes monitoring scan described below, the image processing function 374 converts the X-ray CT image data into monitoring image data by a known method. The image processing function 374 stores the various kinds of converted image data in the memory 35.

The scan control function 375 controls CT scan performed by the platform 10. The scan control function 375 controls the operations of the X-ray high-voltage apparatus 11, the X-ray detector 13, the platform control apparatus 16, the data collection circuit 14, and the couch driving apparatus 21 to control start of scan, execution of scan, and end of scan of the platform 10, for example. Specifically, the scan control function 375 controls projection data collection processing in positioning imaging (positioning scan) collecting positioning image data (scanogram image data) indicating a positioning image (a scanogram image) and full imaging (full scan) collecting image data indicating an image for use in diagnosis based on an examination protocol selected by a user such as a radiologist or a doctor.

The following describes an example of a procedure in which the scan control function 375 receives the examination protocol selected by the user. The scan control function 375 causes the display 32 to display a human body model of the subject P, for example. The user selects a site to be imaged (imaging site, target site to be imaged) via the input interface 31 out of a plurality of sites of the human body model displayed on the display 32. The scan control function 375 then causes the display 32 to display a plurality of preset examination protocols for the site to be imaged selected by the user in a selectable manner. The user selects an examination protocol for use in imaging out of the examination protocols displayed on the display 32 via the input interface 31. The scan control function 375 then receives the examination protocol selected by the user as the examination protocol for use in imaging.

The scan control function 375 can image two-dimensional scanogram image data and three-dimensional scanogram image data. The scan control function 375 fixes the X-ray tube 12a at a 0-degree position (a position in a front direction with respect to the subject P) and continuously performs imaging while moving the couchtop 22 at a constant speed to image the two-dimensional scanogram image data, for example. Alternatively, the scan control function 375 fixes the X-ray tube 12a at the 0-degree position and, while intermittently moving the couchtop 22, intermittently repeats imaging in sync with the movement of the couchtop 22 to image the two-dimensional scanogram image data. The scan control function 375 can image the scanogram image data from not only the front direction with respect to the subject P but also any direction (a side direction, for example). When imaging is performed with the X-ray tube 12a being at a 90-degree position (a position in the side direction with respect to the subject P), for example, imaging from the side of the subject P is performed to obtain the two-dimensional scanogram image. The position of the X-ray tube 12a enables imaging from any plurality of positions if needed.

The scan control function 375 collects the projection data for the total circumference for the subject in the imaging of the scanogram image data to image the three-dimensional scanogram image data. The scan control function 375 collects the projection data for the total circumference for the subject by the helical scan or non-helical scan, for example. The scan control function 375 executes the helical scan or the non-helical scan with a lower dose than that for the full scan for a wide range such as the entire chest, the entire abdomen, the entire upper part of the body, the whole body, or the like of the subject. As the non-helical scan, step-and-shoot type scan is executed, for example.

When an angiographic examination is performed, after a contrast medium is injected into the subject P, the scan control function 375 performs the monitoring scan (monitoring imaging or preparatory scan) for observing the concentration of the contrast medium based on the examination protocol selected by the user. Examples of the contrast medium include an iodine contrast medium. The monitoring scan is imaging observing a change in the concentration of the contrast medium at a region of interest set on a monitoring image as a tomographic image of the subject P. During the monitoring scan, the scan control function 375 detects a CT value that increases in accordance with the concentration of the contrast medium injected into the subject P in the region of interest set on the monitoring image and, with the time when the CT value reaches a threshold as a trigger, shifts to the full scan automatically or after receiving an instruction by the user. Although the monitoring scan does not contribute to diagnosis, it enables shifting to the full scan when the contrast medium is at a high concentration to contribute to improvement in the image quality of the X-ray CT image data to be obtained in the full scan.

The display control function 376 performs control to display images based on the various kinds of image data stored in the memory 35 on the display 32. The display control function 376 causes the display 32 to display the monitoring image based on the monitoring image data, for example.

The acquisition function 377 acquires the information on the imaging mode. The determination function 378 determines a condition on the energy band of the projection data collected from the X-ray detector 13 based on the information on the imaging mode acquired by the acquisition function 377. The acquisition function 377 is an example of an acquisition unit. The determination function 378 is an example of a determination unit. Details of the acquisition function 377 and the determination function 378 will be described below.

The configuration of the X-ray CT apparatus 1 according to the first embodiment has been described. In the photon counting CT, setting of an optimum energy band varies in the imaging mode. Given this, the X-ray CT apparatus 1 according to the first embodiment executes various kinds of processing described below so as to enable the optimum energy band to be determined in accordance with the imaging mode.

Figures 4, 5:
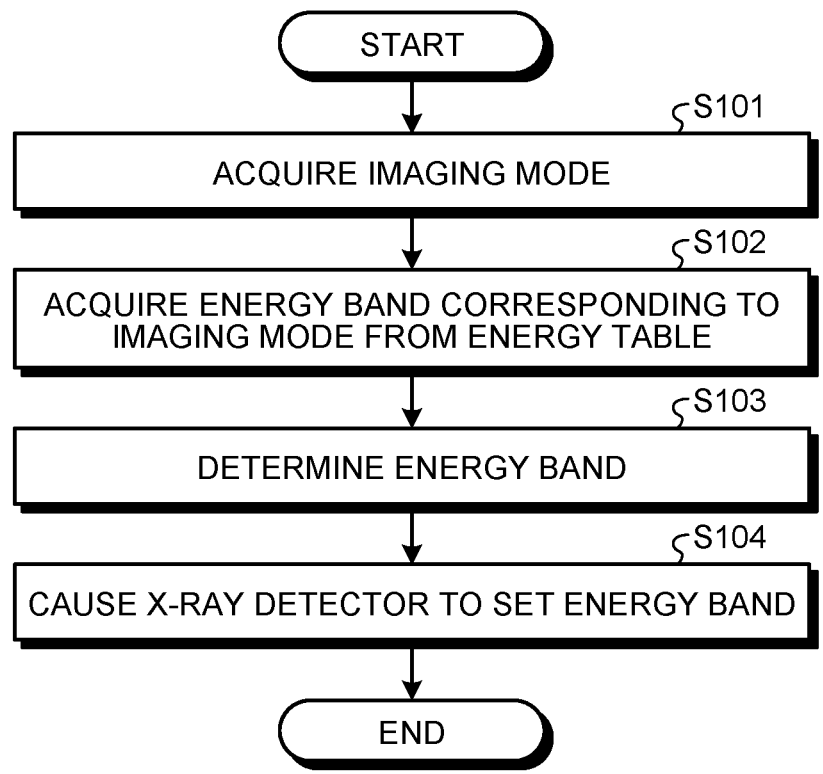
FIG. 4 is a diagram of an example of a data structure of an energy table according to the first embodiment.
FIG. 5 is a flowchart of an example of a procedure of first energy band determination processing that the X-ray CT apparatus according to the first embodiment executes.

FIG. 4 is a diagram of an example of a data structure of the energy table 35a according to the first embodiment. As illustrated in FIG. 4, a plurality of records having items "imaging mode" and "energy band" are registered in the energy table 35a. The imaging mode in the first embodiment indicates various kinds (aims) of imaging such as the monitoring scan, the helical scan in the full scan, and the conventional scan in the full scan, for example.

Information indicating the imaging mode is registered in the item "imaging mode." As illustrated in FIG. 4, "monitoring scan" is registered in the item "imaging mode" of the first record, for example. As illustrated in FIG. 4, "helical scan in full scan" is registered in the item "imaging mode" of the second record. Thus, the information on the imaging mode is registered in the item "imaging mode."

An optimum energy band corresponding to the imaging mode registered in the item "imaging mode" is registered in the item "energy band." In the monitoring scan, for example, it is sufficient to check the concentration of the iodine contrast medium. For the iodine contrast medium, its contrast effect is emphasized by a relatively low energy band (an energy band with the energy value $41b$ or more and less than the energy value $41c$, for example). Given this, as illustrated in FIG. 4, an optimum energy band "energy value $41b$ to $41c$" corresponding to "monitoring scan" is registered in the item "energy band" of the first record. This energy band "energy value $41b$ to $41c$" indicates the energy band with the energy value $41b$ or more and less than the energy value $41c$.

When the helical scan is executed in the full scan, the X-ray CT apparatus 1 may have to acquire many pieces of energy information in order to obtain clinical information. In this case, it is considered that the number of energy bands is increased so that the range of energy can be maximized and features can be extracted. Given this, as illustrated in FIG. 4, an optimum energy band "energy value $41a$ to $41b$, $41b$ to $41c$, $41c$ to $41d$, $41d$ to $41e$, $41e$ to $41f$, and $41f$ to $41g$" corresponding to "helical scan in full scan" is registered in the item "energy band" of the second record. This energy band "energy value $41a$ to $41b$, $41b$ to $41c$, $41c$ to $41d$, $41d$ to $41e$, $41e$ to $41f$, and $41f$ to $41g$" indicates an energy band with the energy value $41a$ or more and less than the energy value $41b$, the energy band with the energy value $41b$ or more and less than the energy value $41c$, an energy band with the energy value $41c$ or more and less than the energy value $41d$, an energy band with the energy value $41d$ or more and less than the energy value $41e$, an energy band with the energy value $41e$ or more and less than the energy value $41f$, and an energy band with the energy value $41f$ or more and less than the energy value $41g$.

The following describes a procedure of first energy band determination processing that the X-ray CT apparatus 1 executes. The first energy band determination processing is processing for determining the energy band to be used when the X-ray detector 13 generates the digital data described above. FIG. 5 is a flowchart of an example of the procedure of the first energy band determination processing that the X-ray CT apparatus 1 according to the first embodiment executes.

As illustrated in FIG. 5, the acquisition function 377 acquires an imaging mode to be executed (an imaging mode slated to be executed) (Step S101). The memory 35 stores therein the examination protocol selected by the user, for example. The acquisition function 377 acquires the examination protocol selected by the user from the memory 35 and acquires the imaging mode from the acquired examination protocol. The acquisition function 377 acquires "monitoring scan," "helical scan in full scan," or the like as the imaging mode, for example. Thus, the acquisition function 377 acquires the information on the imaging mode.

The determination function 378 acquires an optimum energy band corresponding to the imaging mode acquired at Step S101 from the energy table 35a (Step S102). When the imaging mode "monitoring scan" has been acquired at Step S101, for example, the determination function 378 refers to the energy table 35a to acquire the energy band "energy value $41b$ to $41c$" at Step S102. When the imaging mode "helical scan in full scan" has been acquired at Step S101, the determination function 378 refers to the energy table 35a to acquire the energy band "energy value $41a$ to $41b$, $41b$ to $41c$, $41c$ to $41d$, $41d$ to $41e$, $41e$ to $41f$, and $41f$ to $41g$" at Step S102.

The determination function 378 then determines an energy band corresponding to the energy band acquired at Step S102 out of the six energy bands $40a$ to $40f$ as an energy band when imaging (scan) on the imaging mode acquired at Step S101 is performed (Step S103).

Figure 6:
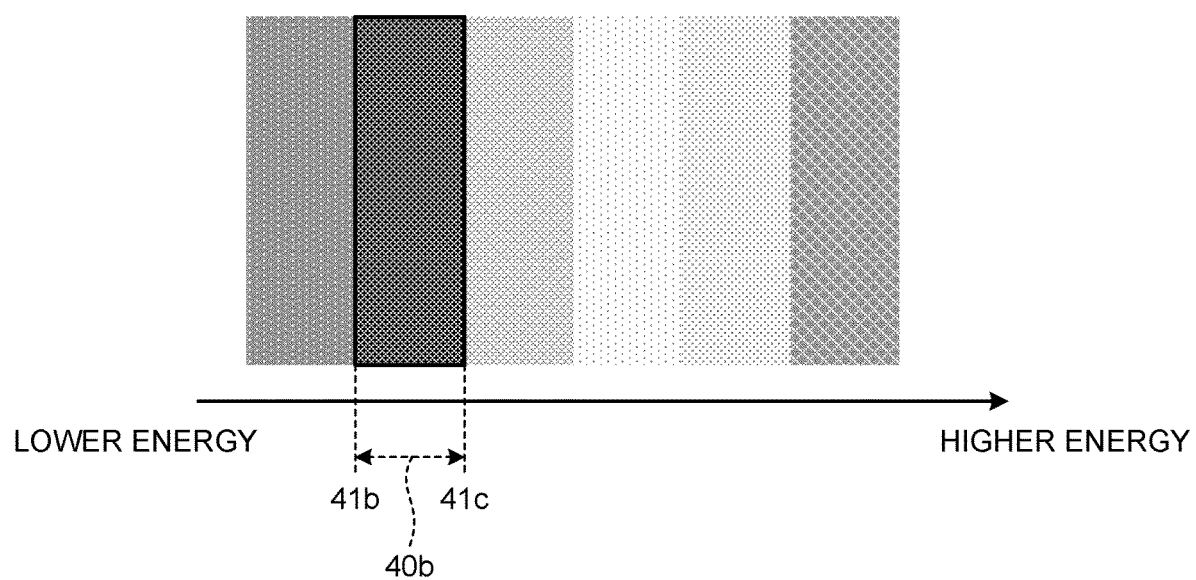
FIG. 6 is a diagram of an example of an energy band determined in the first embodiment.

The following describes a case in which the energy band "energy value $41b$ to $41c$" has been acquired at Step S102, for example. FIG. 6 is a diagram of an example of an energy band determined in the first embodiment. In this case, at Step S103, the determination function 378 determines the energy band $40b$ corresponding to the energy band "energy value $41b$ to $41c$" as an energy band when the monitoring scan is performed as illustrated in FIG. 6.

The following describes a case in which the energy band "energy value 41a to 41b, 41b to 41c, 41c to 41d, 41d to 41e, 41e to 41f, and 41f to 41g" has been acquired at Step S102, for example. In this case, at Step S103, the determination function 378 determines the six energy bands 40a to 40f corresponding to the energy band "energy value 41a to 41b, 41b to 41c, 41c to 41d, 41d to 41e, 41e to 41f, and 41f to 41g" as an energy band when the helical scan is performed in the full scan as illustrated in FIG. 3.

The determination function 378 then causes the X-ray detector 13 to set the energy band determined at Step S103 as the energy band when imaging on the imaging mode acquired at Step S101 is performed (Step S104). When the energy band 40b has been determined at Step S103, for example, the determination function 378 causes the X-ray detector 13 to set the energy band 40b as an energy band when the imaging mode "monitoring scan" is performed at Step S104.

When the energy bands 40a to 40f have been determined at Step S103, the determination function 378 causes the X-ray detector 13 to set the energy bands 40a to 40f as energy bands when the imaging mode "helical scan in full scan" is performed. The determination function 378 then ends the first energy band determination processing.

The following describes the processing at Step S104 with reference to a specific example. The determination function 378 first determines a condition on the energy band of the data collected from the X-ray detector 13, or a first condition, based on the acquired imaging mode at Step S104, for example. This first condition includes the ranges of the respective energy bands, the number of energy bands, and merge information. The merge information includes information indicating whether at least two energy bands out of the energy bands 40a to 40f are merged and, if they are merged, information indicating energy bands to be merged.

When the energy band 40b has been determined at Step S103, for example, the determination function 378 determines the first condition indicating that the range of the energy band is the range of the energy value 41b or more and less than the energy value 41c and that the number of energy bands is "1" at Step S104. The merge information included in this first condition includes information indicating that merging is not performed. The determination function 378 then transmits the determined first condition to the X-ray detector 13 at Step S104.

Upon reception of the first condition, the X-ray detector 13 sets an energy band so as to fit the first condition. The X-ray detector 13 determines one energy band 40b so as to fit the first condition, for example. The X-ray detector 13 then acquires the energy information of the set energy band.

The following describes a case in which the energy band 40b has been set as the energy band when the imaging mode "monitoring scan" is performed in the first energy band determination processing. In this case, in the monitoring scan, the X-ray detector 13 generates digital data indicating an X-ray photon counting result of the energy band 40b out of the six energy bands 40a to 40f and outputs the generated digital data to the data collection circuit 14. In this case, the X-ray detector 13 does not count the X-ray photons of the respective other five energy bands 40a and 40c to 40f. That is to say, the X-ray detector 13 does not generate digital data indicating X-ray photon counting results of the respective five energy bands 40a and 40c to 40f.

The X-ray detector 13 may generate the digital data indicating the X-ray photon counting results of the respective five energy bands 40a and 40c to 40f but not output it and output the digital data indicating the X-ray photon counting result of the energy band 40b. The digital data output from the X-ray detector 13 does not include the X-ray photon counting results of the energy bands 40a and 40c to 40d other than the energy band 40b.

In the photon counting CT imaging, in general, information on the energy band is acquired, and thus the data size (the amount of information) of data output from an X-ray detector tends to be relatively large. However, the first embodiment optimizes the energy band in accordance with the imaging mode and can thereby reduce an increase in the data size of the digital data output from the X-ray detector 13. By extension, an increase in the data size of the raw data stored in the memory 35 of the console 30 can be reduced.

Figure 7:
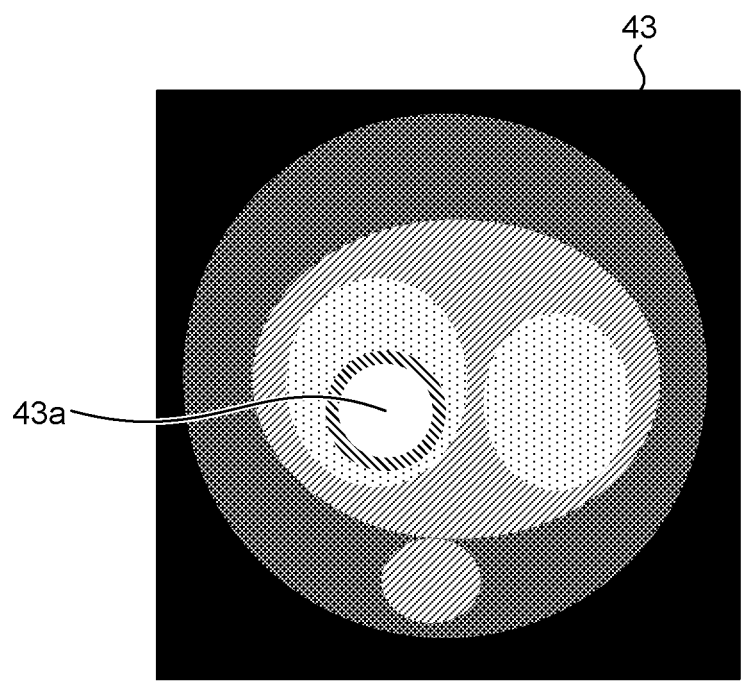
FIG. 7 is a diagram of an example of a monitoring image based on monitoring image data according to the first embodiment.

The digital data indicating the X-ray photon counting result of the energy band 40b passes through the data collection circuit 14, the preprocessing function 372, the reconstruction processing function 373, and the image processing function 374 to become the monitoring image data. The display control function 376 displays the monitoring image based on the monitoring image data on the display 32. FIG. 7 is a diagram of an example of a monitoring image 43 according to the first embodiment. In the monitoring image 43 illustrated in FIG. 7, an iodine contrast medium 43a is clearly delineated. Consequently, the first embodiment determines an effective energy band corresponding to the imaging mode and can thus generate valuable monitoring image data with which the monitoring scan can effectively be performed.

The X-ray CT apparatus 1 according to the first embodiment automatically optimizes the energy band in accordance with the imaging mode. The X-ray CT apparatus 1 automatically determines and sets the optimum energy band 40b out of the six energy bands 40a to 40f, for example. Consequently, the first embodiment can automatically determine the optimum energy band in accordance with the imaging mode. Thus, the first embodiment can reduce a load on the user at the time of setting-up and imaging compared with a case in which the user manually sets the energy band. In addition, improvement in workflow is expected.

In addition, the first embodiment automatically sets the energy band and can thus cause the user to perform a photon counting CT examination with a sensation similar to that for normal CT imaging, which does not cause the user to set the energy band, without causing the user to be conscious that the photon counting CT imaging is being used.

The following describes a case in which the six energy bands 40a to 40f have been set as the energy bands when the imaging mode "helical scan in full scan" is performed in the first energy band determination processing. In this case, in the full scan, the X-ray detector 13 generates digital data indicating X-ray photon counting results of the respective six energy bands 40a to 40f and outputs the generated digital data to the data collection circuit 14.

Figure 8:
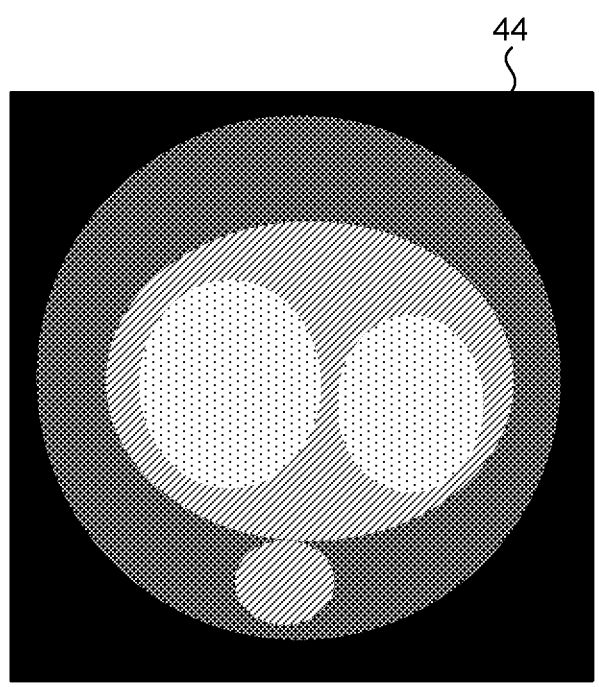
FIG. 8 is a diagram of an example of an image based on image data according to the first embodiment.

This digital data passes through the data collection circuit 14, the preprocessing function 372, the reconstruction processing function 373, and the image processing function 374 to become the image data. The display control function 376 displays the image based on the image data on the display 32. FIG. 8 is a diagram of an example of an image 44 according to the first embodiment. In the image 44 illustrated in FIG. 8, information on many energy bands required for a clinical examination is clearly delineated. Consequently, the first embodiment determines an effective energy band corresponding to the imaging mode and can thus generate valuable image data with which identification or observation of the progress of lesions can effectively be performed.

The X-ray CT apparatus 1 automatically determines and sets the six energy bands 40a to 40f in accordance with the imaging mode. Also owing to this point, a load on the user at the time of setting-up and imaging can be reduced, and improvement in workflow is expected. The X-ray CT apparatus 1 can cause the user to perform a photon counting CT examination with a sensation similar to that for normal CT imaging, which does not cause the user to set the energy band, without causing the user to be conscious that the photon counting CT imaging is being used.

Various imaging modes other than "monitoring scan" and "helical scan in full scan" described above are registered in the item "imaging mode" of the energy table 35a. Thus, various optimum energy bands corresponding to the various other imaging modes are registered in the item "energy band." The following describes specific examples of processing that the determination function 378 executes at Step S103 when having acquired various energy bands at Step S102.

FIGS. 9 to 13 illustrate diagrams for illustrating examples of the processing that the determination function 378 according to the first embodiment executes at Step S103 when having acquired various other energy bands at Step S102.

Figure 9:
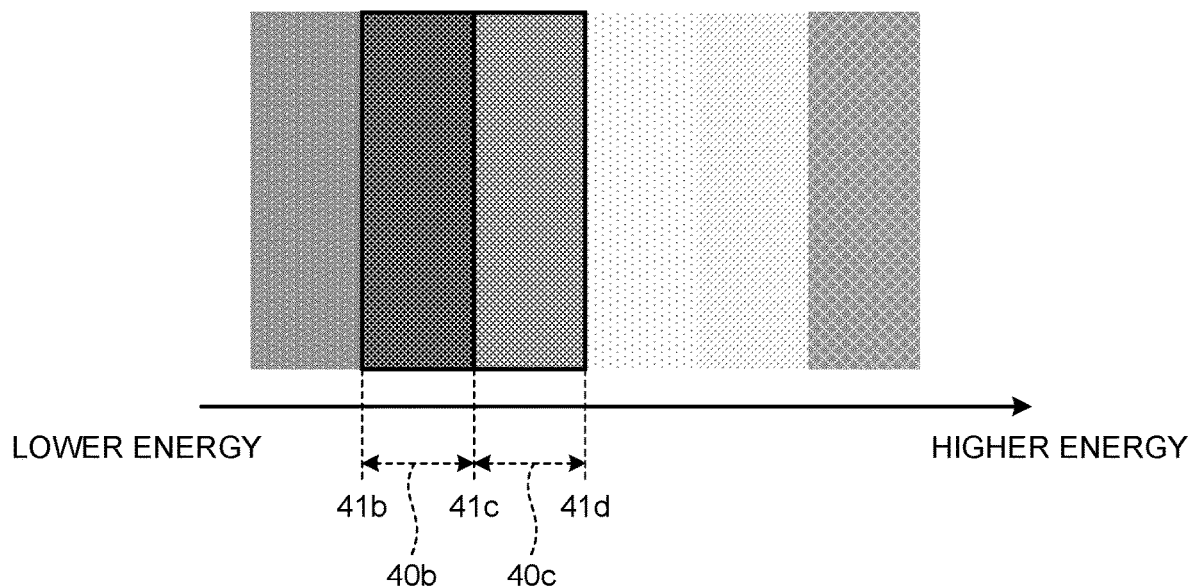
FIG. 9 is a diagram for illustrating an example of processing that a determination function according to the first embodiment executes at Step S103 when having acquired various other energy bands at Step S102.

The following describes a case in which the determination function 378 has acquired an energy band "energy value 41b to 41c and 41c to 41d" at Step S102, for example. This energy band "energy value 41b to 41c and 41c to 41d" indicates the energy band with the energy value 41b or more and less than the energy value 41c and the energy band with the energy value 41c or more and less than the energy value 41d. In this case, at Step S103, as illustrated in FIG. 9, the determination function 378 determines two energy bands 40b and 40c corresponding to the energy band "energy value 41b to 41c and 41c to 41d" as the energy bands when imaging on the imaging mode acquired at Step S101 is performed.

Figure 10:
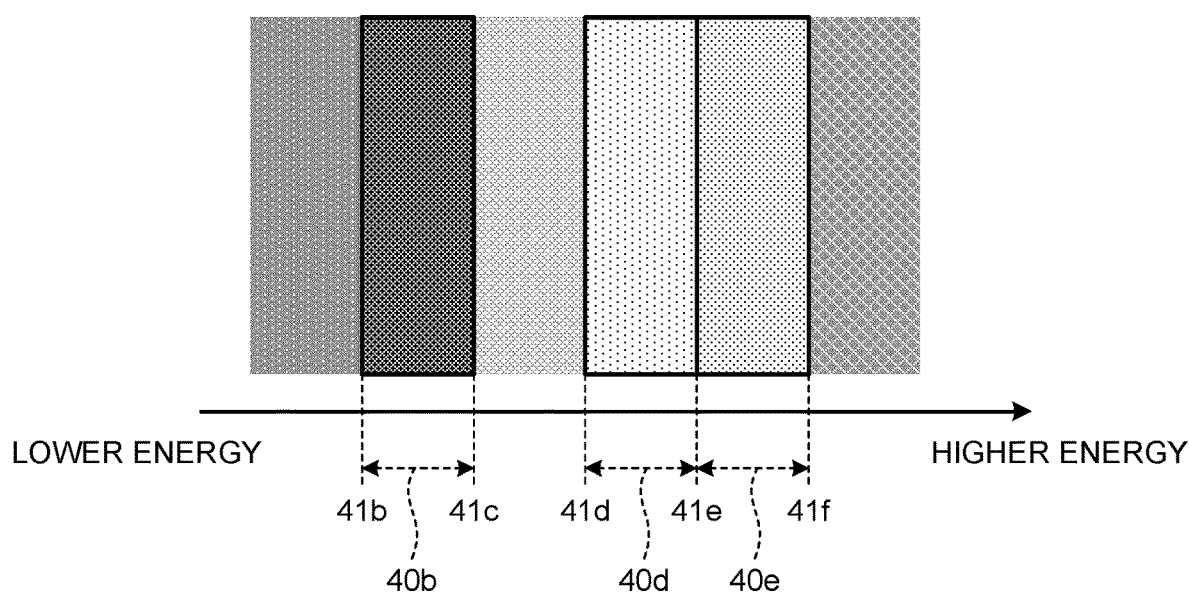
FIG. 10 is a diagram for illustrating an example of the processing that the determination function according to the first embodiment executes at Step S103 when having acquired various other energy bands at Step S102.

The following describes a case in which the determination function 378 has acquired an energy band "energy value 41b to 41c, 41d to 41e, and 41e to 41f" at Step S102, for example. This energy band "energy value 41b to 41c, 41d to 41e, and 41e to 41f" indicates the energy band with the energy value 41b or more and less than the energy value 41c, the energy band with the energy value 41d or more and less than the energy value 41e, and the energy band with the energy value 41e or more and less than the energy value 41f. In this case, at Step S103, as illustrated in FIG. 10, the determination function 378 determines three energy bands 40b, 40d, and 40e corresponding to the energy band "energy value 41b to 41c, 41d to 41e, and 41e to 41f" as the energy bands when imaging on the imaging mode acquired at Step S101 is performed.

Figure 11:
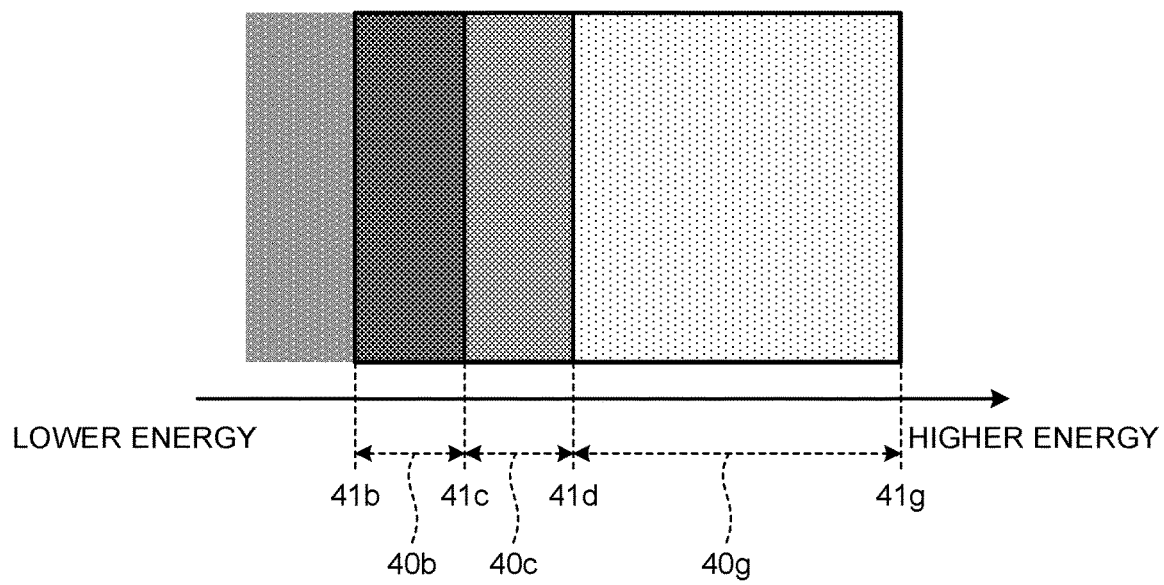
FIG. 11 is a diagram for illustrating an example of the processing that the determination function according to the first embodiment executes at Step S103 when having acquired various other energy bands at Step S102.

The following describes a case in which the determination function 378 has acquired an energy band "energy value 41b to 41c, 41c to 41d, and 41d to 41g" at Step S102, for example. This energy band "energy value 41b to 41c, 41c to 41d, and 41d to 41g" indicates the energy band with the energy value 41b or more and less than the energy value 41c, the energy band with the energy value 41c or more and less than the energy value 41d, and an energy band with the energy value 41d or more and less than the energy value 41g. In this case, at Step S103, as illustrated in FIG. 11, the determination function 378 determines three energy bands 40b, 40d, and 40g corresponding to the energy band "energy value 41b to 41c, 41c to 41d, and 41d to 41g" as the energy bands when imaging on the imaging mode acquired at Step S101 is performed. The energy band "energy value 41d to 41g" corresponds to three energy bands 40d to 40f. Given this, the determination function 378 bundles the three energy bands 40d to 40f to make one energy band 40g. That is to say, the determination function 378 makes one energy band obtained by merging the three energy bands 40d to 40f into the energy band 40g.

The following describes the first condition to be transmitted to the X-ray detector 13 at Step S104 in this case. This first condition includes the following ranges for each energy band: the range of the first energy band is the range of the energy value 41b or more and less than the energy value 41c, the range of the second energy band is the range of the energy value 41c or more and less than the energy value 41d, the range of the third energy band is a range of the energy value 41d or more and less than the energy value 41g. The first condition includes that the number of energy bands is "3." The merge information included in the first condition includes information indicating that the three energy bands 40d, 40e, and 40f are merged.

Upon reception of such a first condition, the X-ray detector 13 sets energy bands so as to fit the first condition. The X-ray detector 13 sets three energy bands 40b, 40c, and 40g so as to fit the first condition, for example. The X-ray detector 13 merges the three energy bands 40d, 40e, and 40f to set the one energy band 40g. The X-ray detector 13 then acquires the energy information of the set three energy bands 40b, 40c, and 40g.

Figure 12:
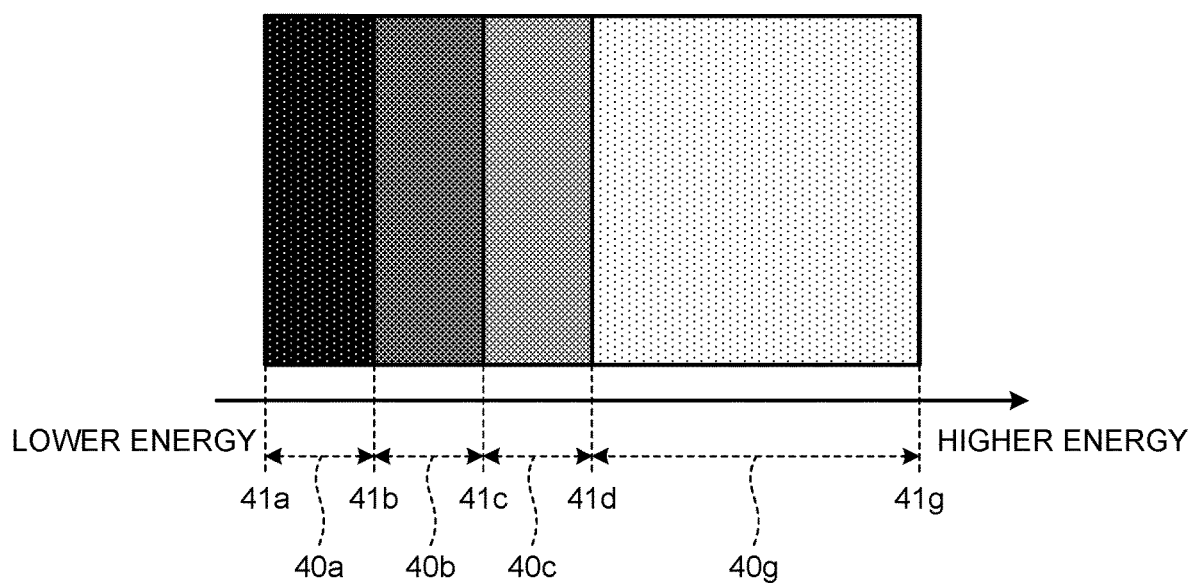
FIG. 12 is a diagram for illustrating an example of the processing that the determination function according to the first embodiment executes at Step S103 when having acquired various other energy bands at Step S102.

The following describes a case in which the determination function 378 has acquired an energy band "energy value 41a to 41b, 41b to 41c, 41c to 41d, and 41d to 41g" at Step S102, for example. This energy band "energy value 41a to 41b, 41b to 41c, 41c to 41d, and 41d to 41g" indicates the energy band with the energy value 41a or more and less than the energy value 41b, the energy band with the energy value 41b or more and less than the energy value 41c, the energy band with the energy value 41c or more and less than the energy value 41d, and the energy band with the energy value 41d or more and less than the energy value 41g. In this case, at Step S103, as illustrated in FIG. 12, the determination function 378 determines four energy bands 40a, 40b, 40d, and 40g corresponding to the energy band "energy value 41a to 41b, 41b to 41c, 41c to 41d, and 41d to 41g" as the energy bands when imaging on the imaging mode acquired at Step S101 is performed.

Figure 13:
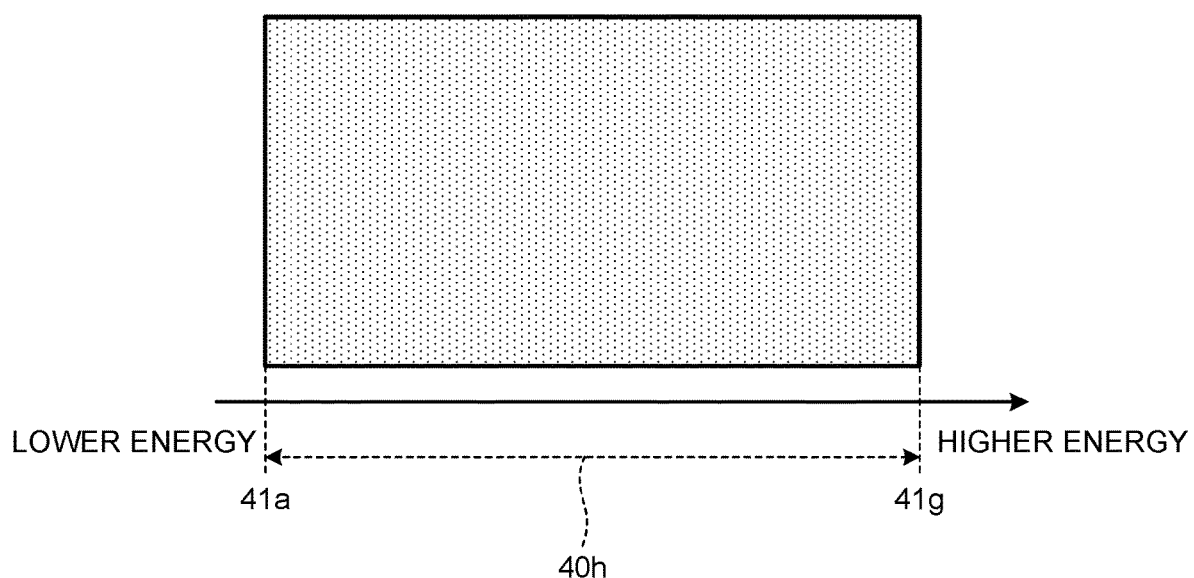
FIG. 13 is a diagram for illustrating an example of the processing that the determination function according to the first embodiment executes at Step S103 when having acquired various other energy bands at Step S102.

The following describes a case in which the determination function 378 has acquired an energy band "energy value 41a to 41g" at Step S102, for example. This energy band "energy value 41a to 41g" indicates an energy band with the energy value 41a or more and less than the energy value 41g. In this case, at Step S103, as illustrated in FIG. 13, the determination function 378 determines one energy band 40h corresponding to the energy band "energy value 41a to 41g" as the energy band when imaging on the imaging mode acquired at Step S101 is performed. The energy band "energy value 41a to 41g" corresponds to the six energy bands 40a to 40f. Given this, the determination function 378 bundles the six energy bands 40a to 40f to make one energy band 40h. That is to say, the determination function 378 makes one energy band obtained by merging the six energy bands 40a to 40f into the energy band 40h.

The X-ray CT apparatus 1 according to the first embodiment has been described. The first embodiment can determine the optimum energy band corresponding to the imaging mode as described above.

Modification of First Embodiment

The first embodiment described above has described a case in which the X-ray CT apparatus 1 determines the optimum energy band in accordance with the imaging mode. Now, the X-ray CT apparatus 1 can perform CT fluoroscopy. CT fluoroscopy is a method of imaging continuously applying X-rays based on a lower tube current than that for the full scan to the subject P to generate image data of the region of interest of the subject P in real time. CT fluoroscopy is performed in order to guide a medical device such as a puncture needle for use in biopsy, for example. The X-ray CT apparatus 1 may determine the optimum energy band in accordance with the type of the medical device for use in an examination. Given this, the following describes such a modification as a modification of the first embodiment. The description of the modification of the first embodiment mainly describes points different from those of the first embodiment and may omit descriptions of components similar to those of the first embodiment.

Figures 14, 15:
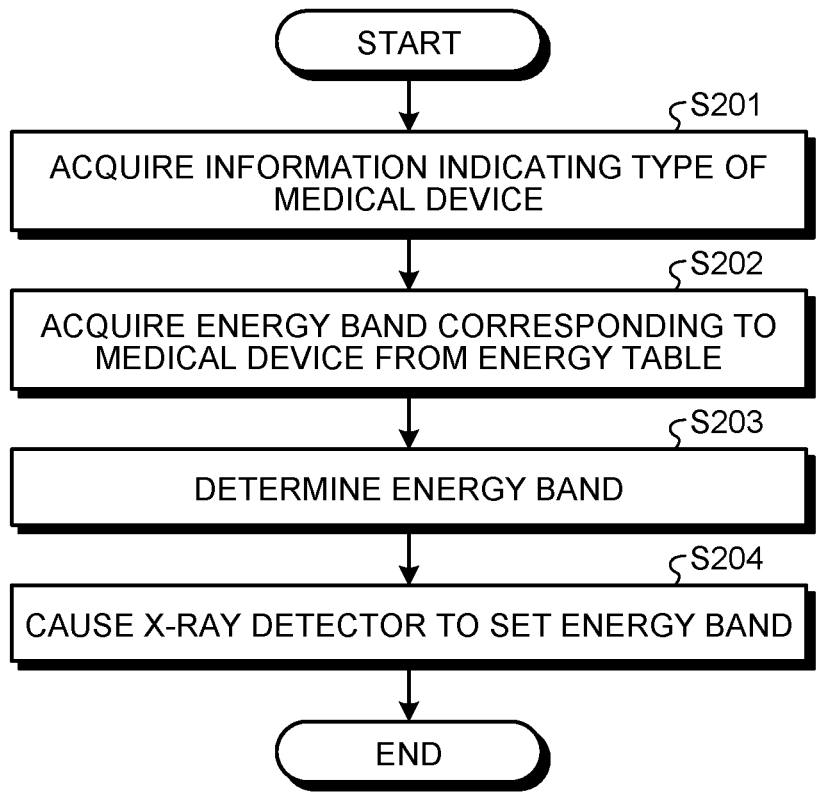
FIG. 14 is a diagram of an example of a data structure of an energy table according to a modification of the first embodiment.
FIG. 15 is a flowchart of an example of a procedure of second energy band determination processing that the X-ray CT apparatus according to the modification of the first embodiment executes.

FIG. 14 is a diagram of an example of a data structure of an energy table 35b according to the modification of the first embodiment. In the modification of the first embodiment, the memory 35 stores therein the energy table 35b illustrated in FIG. 14. As illustrated in FIG. 14, a plurality of records having items "medical device" and "energy band" are registered in the energy table 35b.

Information indicating the type of a medical device used at the time of imaging is registered in the item "medical device." As illustrated in FIG. 14, "puncture needle" is registered in the item "medical device" of the first record, for example. Thus, the information on the medical device is registered in the item "medical device."

An optimum energy band corresponding to the type of the medical device indicated by the information registered in the item "medical device" is registered in the item "energy band." In CT fluoroscopy, the puncture needle is preferably clearly delineated on an image displayed on the display 32, for example. Energy bands causing the puncture needle to be clearly delineated on the image are the energy band with the energy value 41b or more and less than the energy value 41c and the energy band with the energy value 41c or more and less than the energy value 41d, for example. In this case, as illustrated in FIG. 14, the optimum energy band "energy value 41b to 41c and 41c to 41d" corresponding to "puncture needle" is registered in the item "energy band" of the first record.

The following describes a procedure of second energy band determination processing that the X-ray CT apparatus 1 executes in the modification of the first embodiment. The second energy band determination processing is processing for determining the energy band to be used when the X-ray detector 13 generates the digital data described above. FIG. 15 is a flowchart of an example of the procedure of the second energy band determination processing that the X-ray CT apparatus 1 according to the modification of the first embodiment executes.

As illustrated in FIG. 15, the acquisition function 377 acquires the information indicating the type of the medical device used at the time of imaging (Step S201). The memory 35 stores therein the information indicating the type of the medical device used at the time of imaging, for example. The acquisition function 377 acquires the information indicating the type of the medical device used at the time of imaging from the memory 35. The acquisition function 377 acquires information indicating the puncture needle, for example. Thus, the acquisition function 377 acquires the information on the medical device.

The determination function 378 acquires an optimum energy band corresponding to the type of the medical device indicated by the information acquired at Step S201 from the energy table 35b (Step S202). When the information indicating the puncture needle has been acquired at Step S201, for example, the determination function 378 refers to the energy table 35b to acquire the energy band "energy value 41b to 41c and 41c to 41d" at Step S202.

The determination function 378 then determines an energy band corresponding to the energy band acquired at Step S202 out of the six energy bands 40a to 40f as an energy band when imaging (scan) using the medical device of the type indicated by the information acquired at Step S201 is performed (Step S203). The following describes a case in which the energy band "energy value 41b to 41c and 41c to 41d" has been acquired at Step S202. In this case, at Step S203, as illustrated in FIG. 9, the determination function 378 determines the two energy bands 40b and 40c corresponding to the energy band "energy value 41b to 41c and 41c to 41d" as energy bands when imaging (CT fluoroscopy) using the puncture needle is performed.

The determination function 378 then causes the X-ray detector 13 to set the energy band determined at Step S203 as the energy band when imaging using the medical device of the type indicated by the information acquired at Step S201 is performed (Step S204). When the two energy bands 40b and 40c have been determined at Step S203, for example, the determination function 378 causes the X-ray detector 13 to set the two energy bands 40b and 40c as the energy bands when CT fluoroscopy using the puncture needle is performed at Step S204. The determination function 378 then ends the second energy band determination processing.

The determination function 378 first determines the first condition based on the type of the medical device indicated by the acquired information at Step S204, for example. The determination function 378 then transmits the determined first condition to the X-ray detector 13 at Step S204.

The X-ray CT apparatus 1 according to the modification of the first embodiment has been described. The modification of the first embodiment optimizes the energy band in accordance with the type of the medical device for use in imaging and can thereby reduce an increase in the data size of the digital data output from the X-ray detector 13. By extension, an increase in the data size of the raw data stored in the memory 35 of the console 30 can be reduced.

In the modification of the first embodiment, the display 32 displays the image on which the puncture is clearly delineated in CT fluoroscopy, for example. Consequently, the modification of the first embodiment determines an effective energy band corresponding to the type of the medical device and can thus generate valuable image data with which CT fluoroscopy can effectively be performed.

The X-ray CT apparatus 1 according to the modification of the first embodiment automatically optimizes the energy band in accordance with the type of the medical device. Specifically, the X-ray CT apparatus 1 automatically determines and sets the two optimum energy bands 40b and 40c out of the six energy bands 40a to 40f, for example. Consequently, the modification of the first embodiment can automatically determine the optimum energy band in accordance with the type of the medical device. Thus, the modification of the first embodiment can reduce a load on the user at the time of setting-up and imaging compared with a case in which the user manually sets the energy band. In addition, improvement in workflow is expected. The modification of the first embodiment automatically sets the energy band and can thus cause the user to perform a photon counting CT examination with a sensation similar to that for normal CT imaging, which does not cause the user to set the energy band, without causing the user to be conscious that the photon counting CT imaging is being used.

Second Embodiment

The first embodiment described above has described a case in which the X-ray CT apparatus 1 determines the optimum energy band in accordance with the imaging mode. The modification of the first embodiment described above has described a case in which the X-ray CT apparatus 1 determines the optimum energy band in accordance with the type of the medical device. However, the X-ray CT apparatus 1 may determine the optimum energy band in accordance with a site to be image. Given this, the following describes such an embodiment as a second embodiment. The description of the second embodiment mainly describes points different from those of the first embodiment and the modification of the first embodiment and may omit descriptions of components similar to those of the first embodiment and the modification of the first embodiment.

Figures 16, 17:
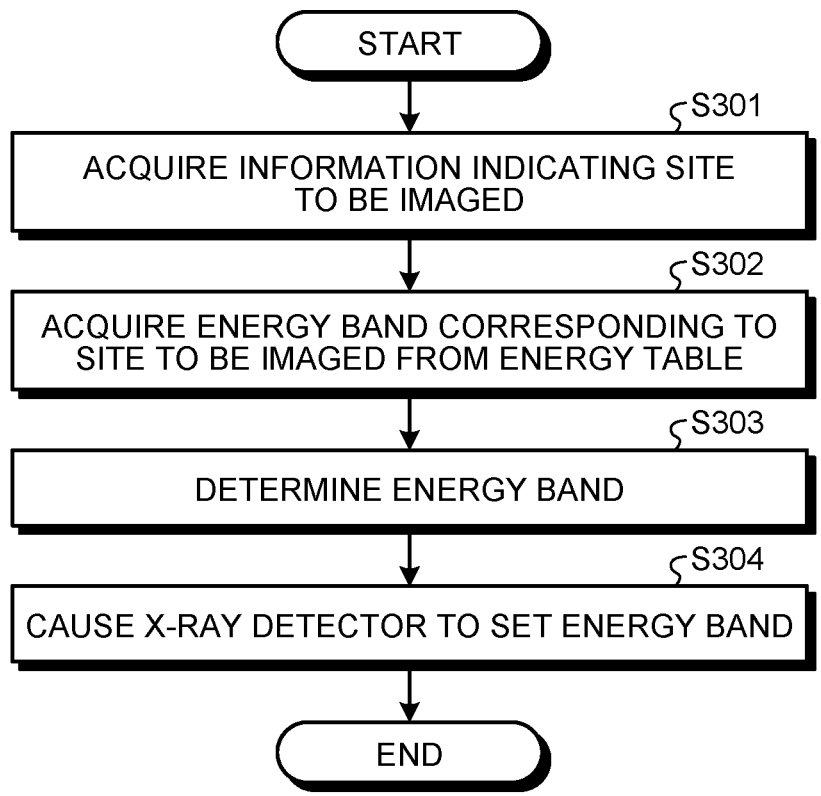
FIG. 16 is a diagram of an example of a data structure of an energy table according to a second embodiment.
FIG. 17 is a flowchart of an example of a procedure of third energy band determination processing that the X-ray CT apparatus according to the second embodiment executes.

FIG. 16 is a diagram of an example of a data structure of an energy table 35c according to the second embodiment. As illustrated in FIG. 16, a plurality of records having items "site to be imaged" and "energy band" are registered in the energy table 35c.

Information indicating the site to be imaged is registered in the item "site to be imaged." As illustrated in FIG. 16, "chest" is registered in the item "site to be imaged" of the first record, for example. "Head" is registered in the item "site to be imaged" of the second record. Thus, the information on the site to be imaged is registered in the item "site to be imaged."

An optimum energy band corresponding to the site to be imaged indicated by the information registered in the item "site to be imaged" is registered in the item "energy band." The following describes a case in which the chest of the subject P is imaged, for example. The soft issue of the chest is preferably clearly delineated on the image based on the image data obtained in this case. An energy band causing the soft issue of the chest to be clearly delineated on the image is the energy band with the energy value 41a or more and less than the energy value 41b, for example. Thus, as illustrated in FIG. 16, the optimum energy band "energy value 41a to 41b" corresponding to "chest" is registered in the item "energy band" of the first record. This energy band "energy value 41a to 41b" indicates the energy band with the energy value 41a or more and less than the energy value 41b.

The following describes a case in which the head of the subject P is imaged, for example. In this case, the beam hardening effect by the skull is preferably reduced. An energy band causing the beam hardening effect by the skull to be reduced is the energy band with the energy value 41c or more and less than the energy value 41d, for example. Thus, as illustrated in FIG. 16, the optimum energy band "energy value 41c to 41d" corresponding to the "head" is registered in the item "energy value" of the second record. This energy band "energy value 41c to 41d" indicates the energy band with the energy value 41c or more and less than the energy value 41d.

The following describes a procedure of third energy determination processing that the X-ray CT apparatus 1 executes in the second embodiment. The third energy determination processing is processing for determining the energy band to be used when the X-ray detector 13 generates the digital data described above. FIG. 17 is a flowchart of an example of the procedure of the third energy band determination processing that the X-ray CT apparatus 1 according to the second embodiment executes.

As illustrated in FIG. 17, the acquisition function 377 acquires the information indicating the site to be imaged (Step S301). The acquisition function 377 may acquire the information indicating the site to be imaged selected by the user out of the sites of the human body model displayed on the display 32 as described above, for example. The acquisition function 377 may perform recognition processing automatically recognizing a site of the subject P delineated on the scanogram image data on the scanogram image data and acquire information indicating the recognized site as the information indicating the site to be imaged. The acquisition function 377 may receive the information indicating the site to be imaged from the user via the input interface 31 to acquire the information indicating the site to be imaged. Thus, the acquisition function 377 acquires the information on the site to be imaged.

The determination function 378 acquires an optimum energy band corresponding to the site to be imaged indicated by the information acquired at Step S301 from the energy table 35c (Step S302). When the information indicating the chest has been acquired at Step S301, for example, the determination function 378 refers to the energy table 35c to acquire the energy band "energy value 41a to 41b" at Step S302. When the information indicating the head has been acquired at Step S301, the determination function 378 refers to the energy table 35c to acquire the energy band "energy value 41c to 41d" at Step S302.

The determination function 378 then determines an energy band corresponding to the energy band acquired at Step S302 out of the six energy bands 40a to 40f as an energy band when the site to be imaged indicated by the information acquire at Step S301 is imaged (Step S303). The following describes a case in which the energy band "energy value 41a to 41b" has been acquired at Step S302. In this case, at Step S303, the determination function 378 determines one energy band 40a corresponding to the energy band "energy value 41a to 41b" as an energy band when the chest is imaged.

The following describes a case in which the energy band "energy value 41c to 41d" has been acquired at Step S302. In this case, at Step S303, the determination function 378 determines one energy band 40c corresponding to the energy band "energy value 41c to 41d" as an energy band when the head is imaged.

The determination function 378 then causes the X-ray detector 13 to set the energy band determined at Step S303 as the energy band when the site to be imaged indicated by the information acquired at Step S301 is imaged (Step S304). When the energy band 40a has been determined at Step S303, for example, the determination function 378 causes the X-ray detector 13 to set the energy band 40a as the energy band when the chest is imaged at Step S304. When the energy band 40c has been determined at Step S303, the determination function 378 causes the X-ray detector 13 to set the energy band 40c as the energy band when the head is imaged at Step S304. The determination function 378 then ends the third energy band determination processing.

The determination function 378 first determines the first condition based on the site to be imaged indicated by the acquired information at Step S304, for example. The determination function 378 then transmits the determined first condition to the X-ray detector 13 at Step S304.

The X-ray CT apparatus 1 according to the second embodiment has been described. The second embodiment optimizes the energy band in accordance with the site to be imaged and can thereby reduce an increase in the data size of the digital data output from the X-ray detector 13. By extension, an increase in the data size of the raw data stored in the memory 35 of the console 30 can be reduced.

In the second embodiment, the display 32 displays the image on which the soft tissue of the chest is clearly delineated, for example. The display 32 displays the image in which the beam hardening effect by the skull is reduced. Consequently, the second embodiment determines an effective energy band corresponding to the site to be imaged and can thus generate valuable image data with which a clinical examination can effectively be performed.

The X-ray CT apparatus 1 according to the second embodiment automatically optimizes the energy band in accordance with the site to be imaged. Specifically, the X-ray CT apparatus 1 automatically determines and sets the one optimum energy band 40a, for example. The X-ray CT apparatus 1 automatically determines and sets the one optimum energy band 40c, for example. Consequently, the second embodiment can automatically determine the optimum energy band in accordance with the site to be imaged. Thus, the second embodiment can reduce a load on the user at the time of setting-up and imaging compared with a case in which the user manually sets the energy band. In addition, improvement in workflow is expected. The second embodiment automatically sets the energy band and can thus cause the user to perform a photon counting CT examination with a sensation similar to that for normal CT imaging, which does not cause the user to set the energy band, without causing the user to be conscious that the photon counting CT imaging is being used.

Third Embodiment

The first embodiment, the modification of the first embodiment, and the second embodiment described above have described cases in which the X-ray CT apparatus 1 causes the X-ray detector 13 to set the optimum energy band. However, the X-ray CT apparatus 1 may control the reconstruction processing function 373 so as to perform the reconstruction processing using data indicating an X-ray photon counting result of the optimum energy band without causing the X-ray detector 13 to set the optimum energy band. Given this, the following describes such an embodiment as a third embodiment. The description of the third embodiment mainly describes points different from those of the first embodiment, the modification of the first embodiment, and the second embodiment and may omit descriptions of components similar to those of the first embodiment, the modification of the first embodiment, and the second embodiment.

In the third embodiment, when generating the digital data, the X-ray detector 13 uses the six energy bands 40a to 40f as they are. That is to say, in the third embodiment, the X-ray detector 13 generates digital data indicating the X-ray photon counting results of the respective six energy bands 40a to 40f and outputs the generated digital data to the data collection circuit 14.

In the third embodiment, the memory 35 stores therein at least one of the energy table 35a, the energy table 35b, and the energy table 35c described above. The following first describes a case in which the memory 35 stores therein the energy table 35a.

The following describes a procedure of fourth energy band determination processing that the X-ray CT apparatus 1 executes using the energy table 35a. The fourth energy band determination processing is processing for determining an energy band for raw data to be subjected to the reconstruction processing by the reconstruction processing function 373. FIG. 18 is a flowchart of an example of the procedure of the fourth energy band determination processing that the X-ray CT apparatus 1 according to the third embodiment executes.

As illustrated in FIG. 18, the acquisition function 377 and the determination function 378 execute the processing at Steps S101 to S103 in the same manner as the processing at Steps S101 to S103 of the first energy band determination processing. The acquisition function 377 acquires the imaging mode (Step S101), whereas the determination function 378 acquires the optimum energy band corresponding to the imaging mode acquired at Step S101 from the energy table 35a (Step S102), for example. The determination function 378 then determines the energy band corresponding to the energy band acquired at Step S102 out of the six energy bands 40a to 40f as the energy band when imaging on the imaging mode acquired at Step S101 is performed (Step S103).

The determination function 378 then controls the reconstruction processing function 373 so as to execute the reconstruction processing on the raw data indicating the X-ray photon counting result of the energy band determined at Step S103 (Step S110). With the control at Step S110, the reconstruction processing function 373 executes the reconstruction processing on the raw data indicating the X-ray photon counting result of the energy band determined at Step S103 out of the raw data indicating the X-ray photon counting results of the respective six energy bands 40a to 40f to reconstruct the CT image data. The determination function 378 then ends the fourth energy band determination processing.

The following describes the processing at Step S110 with reference to a specific example. The determination function 378 first determines a condition on the energy band for the data for use in the reconstruction processing out of the data collected from the X-ray detector 13 based on the acquired imaging mode, or a second condition, at Step S110, for example. This second information, like the first condition, includes the ranges of the respective energy bands, the number of energy bands, and merge information.

When the energy band 40b has been determined at Step S110, for example, the determination function 378 determines the second condition indicating that the range of the energy band is the range of the energy value 41b or more and less than the energy value 41c and that the number of energy bands is "1" at Step S110. The merge information included in this second condition includes information indicating that merging is not performed. The determination function 378 then transmits the determined second condition to the reconstruction processing function 373 at Step S110.

Upon reception of the second condition, the reconstruction processing function 373 executes the reconstruction processing on the raw data of the energy band fitting the second condition out of the raw data indicating the X-ray photon counting results of the respective six energy bands 40a to 40f to reconstruct the X-ray CT image data. The reconstruction processing function 373 is an example of a reconstruction processing unit.

The following describes a case in which the memory 35 stores therein the energy table 35b. The following describes a procedure of fifth energy band determination processing that the X-ray CT apparatus 1 executes using the energy table 35b. The fifth energy band determination processing is processing for determining an energy band for raw data to be subjected to the reconstruction processing by the reconstruction processing function 373. FIG. 19 is a flowchart of an example of the procedure of the fifth energy band determination processing that the X-ray CT apparatus 1 according to the third embodiment executes.

As illustrated in FIG. 19, the acquisition function 377 and the determination function 378 execute the processing at Steps S201 to S203 in the same manner as the processing at Steps S201 to S203 of the second energy band determination processing. The acquisition function 377 acquires the information indicating the type of the medical device used at the time of imaging (Step S201), whereas the determination function 378 acquires the optimum energy band corresponding to the type of the medical device indicated by the information acquired at Step S201 from the energy table 35b (Step S202), for example. The determination function 378 then determines the energy band corresponding to the energy band acquired at Step S202 out of the six energy bands 40a to 40f as the energy band when imaging using the medical device of the type indicated by the information acquired at Step S201 is performed (Step S203).

The determination function 378 then controls the reconstruction processing function 373 so as to execute the reconstruction processing on the raw data indicating the X-ray photon counting result of the energy band determined at Step S203 (Step S210). The determination function 378 then ends the fifth energy band determination processing.

The following describes the processing at Step S210 with reference to a specific example. The determination function 378 first determines the second condition based on the type of the medical device indicated by the acquired information at Step S210, for example. The determination function 378 then transmits the determined second condition to the reconstruction processing function 373 at Step S210.

The following describes a case in which the memory 35 stores therein the energy table 35c. The following describes a procedure of sixth energy band determination processing that the X-ray CT apparatus 1 executes using the energy table 35c. The sixth energy band determination processing is processing for determining an energy band for raw data to be subjected to the reconstruction processing by the reconstruction processing function 373. FIG. 20 is a flowchart of an example of the procedure of the sixth energy band determination processing that the X-ray CT apparatus 1 according to the third embodiment executes.

As illustrated in FIG. 20, the acquisition function 377 and the determination function 378 execute the processing at Steps S301 to S303 in the same manner as the processing at Steps S301 to S303 of the third energy band determination processing. The acquisition function 377 acquires the information indicating the site to be imaged (Step S301), whereas the determination function 378 acquires the optimum energy band corresponding to the site to be imaged indicated by the information acquired at Step S301 from the energy table 35c (Step S302), for example. The determination function 378 then determines the energy band corresponding to the energy band acquired at Step S302 out of the six energy bands 40a to 40f as the energy band when the site to be imaged indicated by the information acquired at Step S301 is imaged (Step S303).

The determination function 378 then controls the reconstruction processing function 373 so as to execute the reconstruction processing on the raw data indicating the X-ray photon counting result of the energy band determined at Step S303 (Step S310). The determination function 378 then ends the sixth energy band determination processing.

The following describes the processing at Step S310 with reference to a specific example. The determination function 378 first determines the second condition based on the site to be imaged indicated by the acquired information at Step S310, for example. The determination function 378 then transmits the determined second condition to the reconstruction processing function 373 at Step S310.

The X-ray CT apparatus 1 according to the third embodiment has been described. The third embodiment determines an effective energy band corresponding to the imaging mode, the type of the medical device, or the site to be imaged and can thus generate valuable image data with which a clinical examination can effectively be performed.

The X-ray CT apparatus 1 according to the third embodiment automatically optimizes the energy band in accordance with the imaging mode, the type of the medical device, or the site to be imaged. Consequently, the third embodiment can automatically determine the optimum energy band in accordance with the imaging mode, the type of the medical device, or the site to be imaged. Thus, the third embodiment can reduce a load on the user at the time of setting-up and imaging compared with a case in which the user manually sets the energy band. In addition, improvement in workflow is expected. The third embodiment automatically determines the energy band and can thus cause the user to perform a photon counting CT examination with a sensation similar to that for normal CT imaging, which does not cause the user to set the energy band, without causing the user to be conscious that the photon counting CT imaging is being used.

Fourth Embodiment

When imaging is performed using a plurality of energy bands, the X-ray photon counting results may significantly vary by energy band. In such a case, when the reconstruction condition is performed on the raw data of all the energy bands on the same reconstruction condition, noise levels of the X-ray CT image data obtained for the respective energy bands may significantly vary among the energy bands. Consequently, noise levels of the image displayed on the display 32 may significantly vary by energy band. Given this, the X-ray CT apparatus 1 may change the reconstruction condition by energy band so as to make the noise levels of the image uniform among the energy bands. Given this, the following describes such an embodiment as a fourth embodiment. The description of the fourth embodiment mainly describes points different from those of the first embodiment, the modification of the first embodiment, the second embodiment, and the third embodiment and may omit descriptions of components similar to those of the first embodiment, the modification of the first embodiment, the second embodiment, and the third embodiment.

The following describes a case in which the X-ray CT apparatus 1 determines the reconstruction condition for each of the energy bands determined by the determination function 378 in any of the first embodiment, the modification of the first embodiment, the second embodiment, and the third embodiment. Note that the X-ray CT apparatus 1 may determine the reconstruction condition for each of the energy bands set by the user via the input interface 31.

Figure 21:
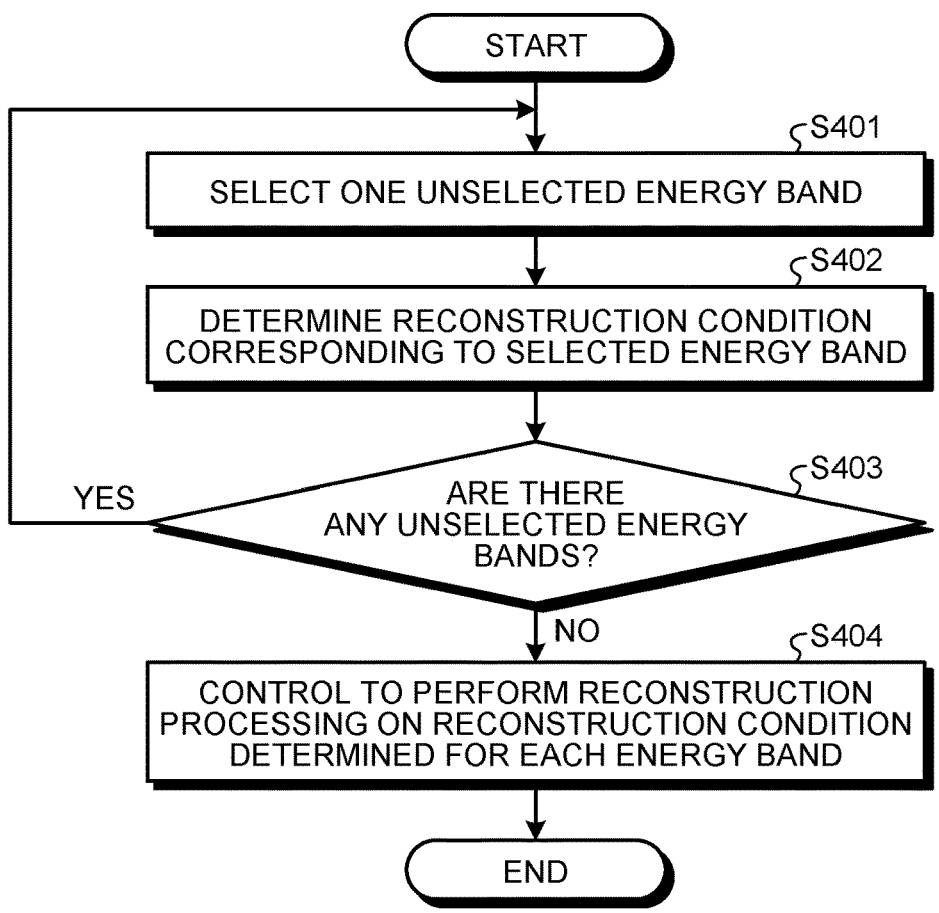
FIG. 21 is a flowchart of an example of a procedure of reconstruction condition determination processing that the X-ray CT apparatus according to a fourth embodiment executes.

The following describes a procedure of reconstruction condition determination processing that the X-ray CT apparatus 1 according to the fourth embodiment executes. The reconstruction condition determination processing is processing for determining an optimum reconstruction condition for each of the energy bands. FIG. 21 is a flowchart of an example of the procedure of the reconstruction condition determination processing that the X-ray CT apparatus 1 according to the fourth embodiment executes.

As illustrated in FIG. 21, the determination function 378 selects one unselected energy band out of the energy bands (Step S401). The determination function 378 then determines an optimum reconstruction condition corresponding to the selected energy band out of a plurality of reconstruction conditions set in advance (Step S402).

The following describes a specific procedure in which the determination function 378 determines the reconstruction condition at Step S402. The following first describes a procedure of the processing at Step S402 when the raw data of the selected energy band has not been collected. An X-ray photon counting result of the selected energy band is predicted in advance, and the memory 35 stores therein the predicted counting result. The determination function 378 acquires the predicted counting result from the memory 35 and determines a reconstruction condition reducing noise in accordance with the X-ray photon counting result indicated by the predicted counting result. The determination function 378 determines the reconstruction condition such that the noise levels of the X-ray CT image data will be constant or substantially constant across all the energy bands, for example. As a specific example, the determination function 378 selects a reconstruction condition having a higher degree of reducing noise for a fewer X-ray photon counting result.

The following describes a procedure of the processing at Step S402 when the raw data of the selected energy band has been collected. The determination function 378 determines a reconstruction condition reducing noise in accordance with the X-ray photon counting result indicated by the collected raw data. The determination function 378 determines the reconstruction condition such that the noise levels of the X-ray CT image data will be constant like the case in which the raw data has not been collected, for example. The determination function 378 selects a reconstruction condition having a higher degree of reducing noise as the X-ray photons counting result decreases, for example.

The determination function 378 then determines whether there are any unselected energy bands in the energy bands (Step S403). If there are any unselected energy bands (Yes at Step S403), the determination function 378 returns to Step S401 and again executes the processing at Step S401 and the subsequent steps. Thus, the determination function 378 performs the processing at Step S402 for all the energy bands to determine reconstruction conditions corresponding to all the respective energy bands.

If there are no unselected energy bands (No at Step S403), the determination function 378 controls the reconstruction processing function 373 so as to perform the reconstruction processing on the raw data indicating the X-ray photon counting results of the respective energy bands on the reconstruction condition determined for each of the energy bands (Step S404).

With the processing at Step S404, the reconstruction processing function 373 performs the reconstruction processing on raw data indicating the X-ray photon counting results of the respective energy bands on the reconstruction condition determined for each of the energy bands to reconstruct the X-ray CT image data. Thus, the X-ray CT image data is reconstructed for each of the energy bands. In the fourth embodiment, the noise levels of the X-ray CT image date reconstructed for each of the energy bands are made uniform. Thus, the fourth embodiment can inhibit the noise levels of the image displayed on the display 32 from significantly varying by energy band.

When a first reconstruction condition and a second reconstruction condition are different from each other, for example, it is considered that the reconstruction processing performed on the first reconstruction condition and the reconstruction processing performed on the second reconstruction condition are pieces of reconstruction processing different from each other. Consequently, in the fourth embodiment, the reconstruction processing function 373 performs different pieces of reconstruction processing in accordance with the energy bands of the data collected from the X-ray detector 13.

Fifth Embodiment

When the raw data of the collected energy bands cannot be stored in the memory 35 in view of the free capacity of the memory 35, the X-ray CT apparatus 1 may narrow down the collected energy bands. Given this, the following describes such an embodiment as a fifth embodiment. The description of the fifth embodiment mainly describes points different from those of the first embodiment, the modification of the first embodiment, the second embodiment, the third embodiment, and the fourth embodiment and may omit descriptions of components similar to those of the first embodiment, the modification of the first embodiment, the second embodiment, the third embodiment, and the fourth embodiment.

Figure 22:
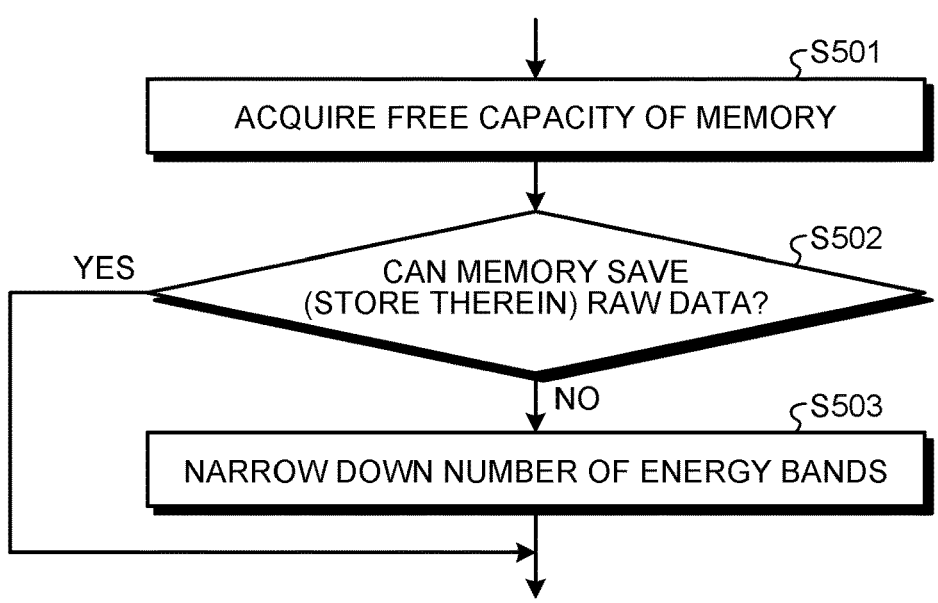
FIG. 22 is a diagram for illustrating an example of processing that the X-ray CT apparatus according to a fifth embodiment executes.

FIG. 22 is a diagram for illustrating an example of processing that the X-ray CT apparatus 1 according to the fifth embodiment executes. The processing at Steps S501 to S503 illustrated in FIG. 22 is executed between Step S103 and Step S104 of the first energy band determination processing illustrated in FIG. 5, for example. The processing at Steps S501 to S503 may be executed between Step S203 and Step S204 of the second energy band determination processing illustrated in FIG. 15. The processing at Steps S501 to S503 may be executed between Step S303 and Step S304 of the third energy band determination processing illustrated in FIG. 17. The processing at Steps S501 to S503 may be executed between Step S103 and Step S110 of the fourth energy band determination processing illustrated in FIG. 18. The processing at Steps S501 to S503 may be executed between Step S203 and Step S210 of the fifth energy band determination processing illustrated in FIG. 19. The processing at Steps S501 to S503 may be executed between Step S303 and Step S310 of the sixth energy band determination processing illustrated in FIG. 20.

At the step immediately before Step S501 illustrated in FIG. 22, or Step S103, S203, or S303, the determination function 378 determines the energy band. As illustrated in FIG. 22, the determination function 378 then acquires the free capacity of the memory 35 (Step S501).

When having collected the projection data using the determined energy band, the determination function 378 determines whether the memory 35 can store the raw data (Step S502). The following describes a specific example of the determination processing at Step S502. At Step S502, the determination function 378 estimates the data size of the raw data to be generated by the preprocessing function 372 when the projection data has been collected using the determined energy band, for example. The determination function 378 then compares the estimated data size of the raw data and the free capacity of the memory 35 with each other and, if the estimated data size of the raw data is larger than the free capacity of the memory 35, determines that the memory 35 cannot store therein the raw data (No at Step S502). In contrast, if the estimated data size of the raw data is not larger than the free capacity of the memory 35, the determination function 378 determines that the memory 35 can store therein the raw data (Yes at Step S502).

If the memory 35 can store therein the raw data (Yes at Step S502), the determination function 378 advances to the next step (Step S104, S204, S304, S110, S210, or S310).

In contrast, if the memory 35 cannot store therein the raw data (No at Step S502), the determination function 378 narrows down the number of energy bands determined at the step immediately before Step S501 (Step S503). The following describes a case in which the two energy bands 40b and 40c illustrated in FIG. 9 have been determined at the step immediately before Step S501, for example. In this case, the determination function 378 narrows down the two energy bands 40b and 40c to one energy band 40b at Step S503.

The determination function 378 then advances to the next step (Step S104, S204, S304, S110, S210, or S310) to perform the processing using the energy band the number of which has been narrowed down at Step S503, not the energy bands determined at the step immediately before Step S501. That is to say, the determination function 378 determines the first condition or the second condition based on the free capacity of the memory 35.

The X-ray CT apparatus 1 according to the fifth embodiment has been described. The fifth embodiment optimizes the energy band and can thereby reduce the data size of the raw data and can store the raw data in the memory 35.

The determination function 378 may cause the display 32 to display a screen for confirming the narrowing down of the number of energy bands with the user before narrowing down the number of energy bands at Step S503. The determination function 378 may narrow down the number of energy bands when an approval for the narrowing down of the number of energy bands is obtained from the user via the input interface 31.

Sixth Embodiment

To generate image data corresponding to the needs of the user, the X-ray CT apparatus 1 may receive a desired reconstruction condition from the user via the input interface 31. Given this, the following describes such an embodiment as a sixth embodiment. The description of the sixth embodiment mainly describes points different from those of the first embodiment, the modification of the first embodiment, the second embodiment, the third embodiment, the fourth embodiment, and the fifth embodiment and may omit descriptions of components similar to those of the first embodiment, the modification of the first embodiment, the second embodiment, the third embodiment, the fourth embodiment, and the fifth embodiment.

Figures 23, 24:
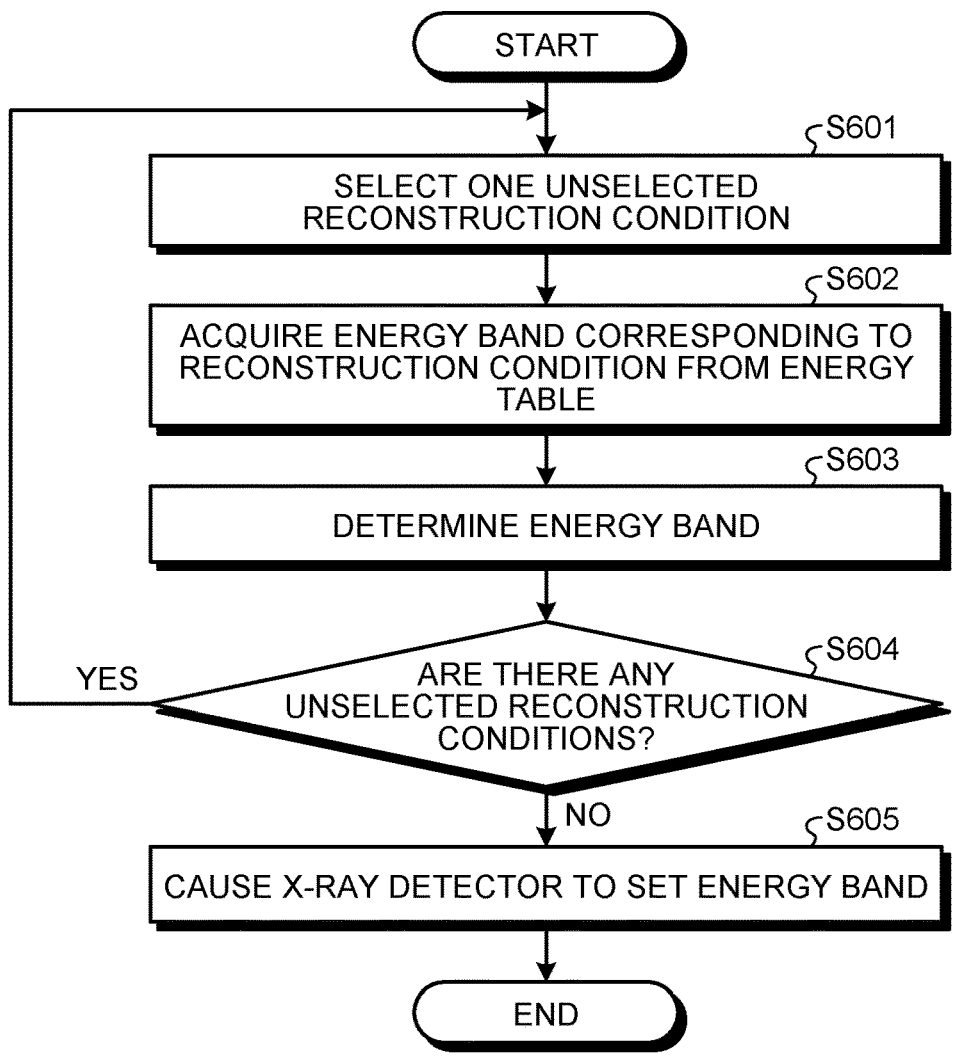
FIG. 23 is a diagram of an example of a data structure of an energy table according to a sixth embodiment.
FIG. 24 is a flowchart of an example of a procedure of seventh energy band determination processing that the X-ray CT apparatus according to the sixth embodiment executes.

FIG. 23 is a diagram of an example of a data structure of an energy table 35d according to the sixth embodiment. As illustrated in FIG. 23, a plurality of records having items "reconstruction condition" and "energy band" are registered in the energy table 35d.

Information indicating the reconstruction condition is registered in the item "reconstruction condition." As illustrated in FIG. 23, a reconstruction condition "AA" is registered in the item "reconstruction condition" of the first record, for example. A reconstruction condition "BB" is registered in the item "reconstruction condition" of the second record. Thus, the information on the reconstruction condition is registered in the item "reconstruction condition."

An optimum energy band corresponding to the reconstruction condition indicated by the information registered in the item "reconstruction condition" is registered in the item "energy band." As illustrated in FIG. 23, an optimum energy band "energy value 41b to 41c" corresponding to the reconstruction condition "AA" is registered in the item "energy band" of the first record, for example. This energy band "energy value 41b to 41c" indicates the energy band with the energy value 41b or more and less than the energy value 41c.

An optimum energy band "energy value 41c to 41d" corresponding to the reconstruction condition "BB" is registered in the item "energy band" of the second record. This energy band "energy value 41c to 41d" indicates the energy band with the energy value 41c or more and less than the energy value 41d.

The following describes a procedure of seventh energy band determination processing that the X-ray CT apparatus 1 executes in the sixth embodiment. The seventh energy band determination processing is processing for determining the energy band to be used when the X-ray detector 13 generates the digital data described above. FIG. 24 is a flowchart of an example of the procedure of the seventh energy band determination processing that the X-ray CT apparatus 1 according to the sixth embodiment executes.

In the sixth embodiment, before the seventh energy band determination processing illustrated in FIG. 24 is executed, one or more desired reconstruction conditions are received from the user via the input interface 31. The user inputs one or more desired reconstruction conditions via the input interface 31 such that image data indicating an image meeting the preference of the user will be generated, for example. The desired reconstruction conditions received by the input interface 31 are examples of input information on a reconstruction condition. The input interface 31 is an example of a reception unit.

As illustrated in FIG. 24, the determination function 378 selects one unselected reconstruction condition out of the one or more reconstruction conditions received by the input interface 31 (Step S601).

The determination function 378 then acquires an optimum energy band corresponding to the reconstruction condition selected at Step S601 from the energy table 35d (Step S602).

The determination function 378 then determines an energy band corresponding to the energy band acquired at Step S602 out of the six energy bands 40a to 40f as an energy band used when the projection image is collected (Step S603).

The determination function 378 then determines whether there are any unselected reconstruction conditions in the one or more reconstruction conditions received by the input interface 31 (Step S604). If there are any unselected reconstruction conditions (Yes at Step S604), the determination function 378 returns to Step S601 and again performs the processing at Step S601 and the subsequent steps. Thus, the determination function 378 performs the processing at Steps S602 and S603 for all the reconstruction conditions to determine optimum energy bands corresponding to all the respective reconstruction conditions.

If there are no unselected reconstruction conditions (No at Step S604), the determination function 378 causes the X-ray detector 13 to set the energy band determined for each of the reconstruction conditions as the energy band used when the projection image is collected (Step S605). That is to say, at Step S605, the determination function 378 determines the first condition on the energy band of the data collected from the X-ray detector 13 based on the desired reconstruction condition. The determination function 378 then ends the seventh energy band determination processing.

The X-ray CT apparatus 1 according to the sixth embodiment has been described. The sixth embodiment optimizes the energy band in accordance with the desired reconstruction condition of the user and can thereby reduce an increase in the data size of the digital data output from the X-ray detector 13. By extension, an increase in the data size of the raw data stored in the memory 35 of the console 30 can be reduced.

The sixth embodiment determines an effective energy band corresponding to the desired reconstruction condition and can thus generate valuable image data with which a clinical examination can effectively be performed.

The X-ray CT apparatus 1 according to the sixth embodiment automatically optimizes the energy band in accordance with the desired reconstruction condition. Consequently, the sixth embodiment can automatically determine the optimum energy band in accordance with the desired reconstruction condition. Thus, the sixth embodiment can reduce a load on the user at the time of setting-up and imaging compared with a case in which the user manually sets the energy band. In addition, improvement in workflow is expected. The sixth embodiment automatically sets the energy band and can thus cause the user to perform a photon counting CT examination with a sensation similar to that for normal CT imaging, which does not cause the user to set the energy band, without causing the user to be conscious that the photon counting CT is being used.

Cases in which the X-ray detector 13 cannot set any optional energy bands have been described in the first embodiment, the modification of the first embodiment, the second embodiment, and the sixth embodiment. However, in the first embodiment, the modification of the first embodiment, the second embodiment, and the sixth embodiment, the X-ray detector 13 may be able to set optional energy bands. In this case, the determination function 378 can cause the X-ray detector 13 to set optional energy bands.

The term "processor" referred to in the above description means a circuit such as a central processing unit (CPU), a graphics processing unit (GPU), an application specific integrated circuit (ASIC), a programmable logic device (a simple programmable logic device (SPLD) or a complex programmable logic device (CPLD), for example), or a field programmable gate array (FPGA), for example. The processor reads and executes a computer program saved in the memory 35 to implement its function. In place of saving the computer program in the memory 35, the computer program may directly be incorporated into the circuit of the processor. In this case, the processor reads and executes the computer program incorporated into the circuit to implement its function. The processors of the present embodiments are not limited to a case in which each of the processors includes a single circuit, and a plurality of independent circuits may be combined to form one processor and to implement its function.

The X-ray CT apparatus 1 of at least one embodiment or at least one modification described above can determine the optimum energy band in accordance with the imaging mode, the site to be imaged, or the type of the medical device.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

Concerning the foregoing embodiments, the following notes are disclosed as aspects and selective features of the invention.

Note 1. A photon counting computed tomography (CT) apparatus comprising:

a photon counting detector configured to detect X-ray photons to acquire energy information;

an acquisition unit configured to acquire at least one piece of information out of information on an imaging mode, information on a site to be imaged, and information on a medical device; and a determination unit configured to, based on the acquired information acquired by the acquisition unit, determine at least one condition out of a first condition on an energy band of data collected from the photon counting detector and a second condition on an energy band for data for use in reconstruction processing out of the data collected from the photon counting detector.

Note 2. The photon counting detector may acquire the energy information of an energy band fitting the first condition determined by the determination unit.

Note 3. The photon counting CT apparatus may further comprise a reconstruction processing unit executing the reconstruction processing on data of an energy band fitting the second condition determined by the determination unit out of the data collected by the photon counting detector to reconstruct X-ray CT image data.

Note 4. The photon counting CT apparatus may further comprise a storage unit storing therein the data collected from the photon counting detector. The determination unit may determine at least one condition out of the first condition and the second condition further based on free capacity of the storage unit.

Note 5. The photon counting detector may set an energy band fitting the first condition and acquire the energy information of the set energy band.

Note 6. The photon counting detector may set the energy band fitting the first condition by merging a plurality of energy bands and acquire the energy information of the set energy band.

Note 7. A photon counting CT apparatus comprising:

a photon counting detector configured to detect X-ray photons to acquire energy information; and a reconstruction processing unit configured to perform different pieces of reconstruction processing in accordance with a plurality of energy bands of data collected from the photon counting detector.

Note 8. A photon counting CT apparatus comprising:

a photon counting detector configured to detect X-ray photons to acquire energy information;

a reception unit configured to receive input information on a desired reconstruction condition; and a determination unit configured to, based on the input information, determine a condition on an energy band of data collected from the photon counting detector.

What is claimed is:

1. A photon counting computed tomography (CT) apparatus comprising:
    a photon counting detector configured to detect X-ray photons to acquire energy information; and
    processing circuitry
        configured to acquire at least one piece of information out of information on an imaging mode, information on a site to be imaged, and information on a medical device, and
        configured to, based on the acquired information, determine at least one condition out of a first condition on an energy band of data collected from the photon counting detector and a second condition on an energy band for data for use in reconstruction processing out of the data collected from the photon counting detector.

2. The photon counting CT apparatus according to claim 1, wherein the photon counting detector acquires the energy information on an energy band fitting the first condition determined by the processing circuitry.

3. The photon counting CT apparatus according to claim 1, wherein the processing circuitry executes the reconstruction processing to data on an energy band fitting the determined second condition out of the data collected by the photon counting detector to reconstruct X-ray CT image data.

4. The photon counting CT apparatus according to claim 1, further comprising a memory storing therein the data collected from the photon counting detector, wherein the processing circuitry determines at least one condition out of the first condition and the second condition further based on free capacity of the memory.

5. The photon counting CT apparatus according to claim 2, wherein the photon counting detector sets an energy band fitting the first condition and acquires the energy information on the set energy band.

6. The photon counting CT apparatus according to claim 5, wherein the photon counting detector sets the energy band fitting the first condition by merging a plurality of energy bands and acquires the energy information on the set energy band.

* * * * *